US011291254B2

(12) United States Patent
Worm et al.

(10) Patent No.: US 11,291,254 B2
(45) Date of Patent: *Apr. 5, 2022

(54) AEROSOL DELIVERY DEVICE INCLUDING A MOVEABLE CARTRIDGE AND RELATED ASSEMBLY METHOD

(71) Applicant: RAI Strategic Holdings, Inc., Winston-Salem, NC (US)

(72) Inventors: Steven L. Worm, Raleigh, NC (US); David Glen Christopherson, Raleigh, NC (US); Robert Adam Parchman, Fuquay-Varina, NC (US); Raymond Charles Henry, Jr., Cary, NC (US); Bruce Alan Bengtsson, Winston-Salem, NC (US); Frederic Philippe Ampolini, Winston-Salem, NC (US); James William Rogers, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/986,867

(22) Filed: Aug. 6, 2020

(65) Prior Publication Data

US 2020/0359680 A1    Nov. 19, 2020

Related U.S. Application Data

(63) Continuation of application No. 15/882,744, filed on Jan. 29, 2018, now Pat. No. 10,750,778, which is a
(Continued)

(51) Int. Cl.
*A24F 40/95* (2020.01)
*A61M 15/06* (2006.01)
(Continued)

(52) U.S. Cl.
CPC .............. *A24F 40/95* (2020.01); *A24F 15/01* (2020.01); *A24F 40/40* (2020.01); *A24F 40/42* (2020.01);
(Continued)

(58) Field of Classification Search
CPC .......... A61M 15/06; A24F 40/95; A24F 15/01
See application file for complete search history.

(56) References Cited

U.S. PATENT DOCUMENTS

| 1,514,682 A | 11/1924 | Wilson |
| 1,771,366 A | 7/1930 | Wyss et al. |

(Continued)

FOREIGN PATENT DOCUMENTS

| AU | 276250 | 7/1965 |
| CA | 2 641 869 | 5/2010 |

(Continued)

OTHER PUBLICATIONS

N. Yagi et al.; Abstact: *Sterilization using 365 nm UV-LED*; Conf. Proc. IEEE Eng. Med. Biol. Soc.; 2007 (1 page). Downloaded from website on Aug. 21, 2014. http://www.ncbi.nlm.nih.gov/pubmed/18003342.

(Continued)

*Primary Examiner* — Anthony Calandra
(74) *Attorney, Agent, or Firm* — Womble Bond Dickinson (US) LLP

(57) ABSTRACT

The present disclosure relates to aerosol delivery devices. The aerosol delivery devices may include a housing and a cartridge including an atomizer and a reservoir configured to contain an aerosol precursor composition. The cartridge may be configured to move relative to at least a portion of the housing between a retracted configuration and an extended configuration. Related assembly methods are also provided.

18 Claims, 28 Drawing Sheets

Related U.S. Application Data continuation of application No. 14/465,167, filed on Aug. 21, 2014, now Pat. No. 9,913,493.

(51) Int. Cl.
| | |
|---|---|
| *A24F 15/01* | (2020.01) |
| *A24F 40/40* | (2020.01) |
| *A45C 13/16* | (2006.01) |
| *A24F 40/42* | (2020.01) |
| *A24F 40/10* | (2020.01) |

(52) U.S. Cl.
CPC ............. *A45C 13/16* (2013.01); *A61M 15/06* (2013.01); *A24F 40/10* (2020.01)

(56) References Cited

U.S. PATENT DOCUMENTS

| 2,057,353 | A | 10/1936 | Whittemore, Jr. |
|---|---|---|---|
| 2,104,266 | A | 1/1938 | McCormick |
| 3,200,819 | A | 8/1965 | Gilbert |
| 3,479,561 | A | 11/1969 | Janning |
| 4,284,089 | A | 8/1981 | Ray |
| 4,303,083 | A | 12/1981 | Burruss, Jr. |
| 4,735,217 | A | 4/1988 | Gerth et al. |
| 4,848,374 | A | 7/1989 | Chard et al. |
| 4,907,606 | A | 3/1990 | Lilja et al. |
| 4,922,901 | A | 5/1990 | Brooks et al. |
| 4,945,931 | A | 8/1990 | Gori |
| 4,947,874 | A | 8/1990 | Brooks et al. |
| 4,947,875 | A | 8/1990 | Brooks et al. |
| 4,986,286 | A | 1/1991 | Roberts et al. |
| 5,019,122 | A | 5/1991 | Clearman et al. |
| 5,042,510 | A | 8/1991 | Curtiss et al. |
| 5,060,671 | A | 10/1991 | Counts et al. |
| 5,093,894 | A | 3/1992 | Deevi et al. |
| 5,144,962 | A | 8/1992 | Counts et al. |
| 5,249,586 | A | 10/1993 | Morgan et al. |
| 5,261,424 | A | 11/1993 | Sprinkel, Jr. |
| 5,322,075 | A | 6/1994 | Deevi et al. |
| 5,353,813 | A | 10/1994 | Deevi et al. |
| 5,369,723 | A | 11/1994 | Counts et al. |
| 5,372,148 | A | 12/1994 | McCafferty et al. |
| 5,388,574 | A | 2/1995 | Ingebrethsen et al. |
| 5,388,594 | A | 2/1995 | Counts et al. |
| 5,408,574 | A | 4/1995 | Deevi et al. |
| 5,468,936 | A | 11/1995 | Deevi et al. |
| 5,498,850 | A | 3/1996 | Das |
| 5,505,214 | A | 4/1996 | Collins et al. |
| 5,515,842 | A | 5/1996 | Ramseyer et al. |
| 5,530,225 | A | 6/1996 | Hajaligol |
| 5,564,442 | A | 10/1996 | MacDonald et al. |
| 5,591,368 | A | 1/1997 | Fleischhauer et al. |
| 5,649,554 | A | 7/1997 | Sprinkel et al. |
| 5,666,977 | A | 9/1997 | Higgins et al. |
| 5,687,746 | A | 11/1997 | Rose et al. |
| 5,726,421 | A | 3/1998 | Fleischhauer et al. |
| 5,727,571 | A | 3/1998 | Meiring et al. |
| 5,743,251 | A | 4/1998 | Howell et al. |
| 5,799,663 | A | 9/1998 | Gross et al. |
| 5,819,756 | A | 10/1998 | Mielordt |
| 5,865,185 | A | 2/1999 | Collins et al. |
| 5,865,186 | A | 2/1999 | Volsey, II |
| 5,878,752 | A | 3/1999 | Adams et al. |
| 5,894,841 | A | 4/1999 | Voges |
| 5,934,289 | A | 8/1999 | Watkins et al. |
| 5,954,979 | A | 9/1999 | Counts et al. |
| 5,967,148 | A | 10/1999 | Harris et al. |
| 6,040,560 | A | 3/2000 | Fleischhauer et al. |
| 6,053,176 | A | 4/2000 | Adams et al. |
| 6,089,857 | A | 7/2000 | Matsuura et al. |
| 6,095,153 | A | 8/2000 | Kessler et al. |
| 6,125,853 | A | 10/2000 | Susa et al. |
| 6,155,268 | A | 12/2000 | Takeuchi |
| 6,164,287 | A | 12/2000 | White |
| 6,196,218 | B1 | 3/2001 | Voges |
| 6,196,219 | B1 | 3/2001 | Hess et al. |
| 6,598,607 | B2 | 7/2003 | Adiga et al. |
| 6,601,776 | B1 | 8/2003 | Oljaca et al. |
| 6,615,840 | B1 | 9/2003 | Fournier et al. |
| 6,688,313 | B2 | 2/2004 | Wrenn et al. |
| 6,772,756 | B2 | 8/2004 | Shayan |
| 6,803,545 | B2 | 10/2004 | Blake et al. |
| 6,803,550 | B2 | 10/2004 | Sharpe et al. |
| 6,854,461 | B2 | 2/2005 | Nichols |
| 6,854,470 | B1 | 2/2005 | Pu |
| 7,117,867 | B2 | 10/2006 | Cox et al. |
| 7,293,565 | B2 | 11/2007 | Griffin et al. |
| 7,513,253 | B2 | 4/2009 | Kobayashi et al. |
| 7,775,459 | B2 | 8/2010 | Martens, III et al. |
| 7,832,410 | B2 | 11/2010 | Hon |
| 7,845,359 | B2 | 12/2010 | Montaser |
| 7,896,006 | B2 | 3/2011 | Hamano et al. |
| 8,127,772 | B2 | 3/2012 | Montaser |
| 8,314,591 | B2 | 11/2012 | Terry et al. |
| 8,365,742 | B2 | 2/2013 | Hon |
| 8,371,310 | B2 | 2/2013 | Brenneise |
| 8,402,976 | B2 | 3/2013 | Fernando et al. |
| 8,499,766 | B1 | 8/2013 | Newton |
| 8,528,569 | B1 | 9/2013 | Newton |
| 8,550,069 | B2 | 10/2013 | Alelov |
| 8,757,147 | B2 | 6/2014 | Terry et al. |
| 8,851,081 | B2 | 10/2014 | Fernando et al. |
| 9,220,302 | B2 | 12/2015 | DePiano et al. |
| 9,468,234 | B2 | 10/2016 | Fernando et al. |
| 9,491,974 | B2 | 11/2016 | DePiano et al. |
| 9,497,999 | B2 | 11/2016 | Lord |
| 9,532,605 | B2 | 1/2017 | Yamada et al. |
| 9,603,386 | B2 | 3/2017 | Xiang |
| 9,603,388 | B2 | 3/2017 | Fernando et al. |
| 9,717,276 | B2 | 8/2017 | Brammer et al. |
| 9,999,259 | B2 | 6/2018 | Memari et al. |
| 2002/0100487 | A1 | 8/2002 | St. Charles et al. |
| 2002/0146242 | A1 | 10/2002 | Vieira |
| 2003/0226837 | A1 | 12/2003 | Blake et al. |
| 2004/0118401 | A1 | 6/2004 | Smith et al. |
| 2004/0129280 | A1 | 7/2004 | Woodson et al. |
| 2004/0200488 | A1 | 10/2004 | Felter et al. |
| 2004/0226568 | A1 | 11/2004 | Takeuchi et al. |
| 2005/0016550 | A1 | 1/2005 | Katase |
| 2005/0268911 | A1 | 12/2005 | Cross et al. |
| 2006/0016453 | A1 | 1/2006 | Kim |
| 2006/0196518 | A1 | 9/2006 | Hon |
| 2007/0074734 | A1 | 4/2007 | Braunshteyn et al. |
| 2007/0102013 | A1 | 5/2007 | Adams et al. |
| 2007/0215167 | A1 | 9/2007 | Crooks et al. |
| 2008/0085103 | A1 | 4/2008 | Beland et al. |
| 2008/0092912 | A1 | 4/2008 | Robinson et al. |
| 2008/0257367 | A1 | 10/2008 | Paterno et al. |
| 2008/0276947 | A1 | 11/2008 | Martzel |
| 2008/0302374 | A1 | 12/2008 | Wengert et al. |
| 2009/0095311 | A1 | 4/2009 | Hon |
| 2009/0095312 | A1 | 4/2009 | Heibrich et al. |
| 2009/0126745 | A1 | 5/2009 | Hon |
| 2009/0188490 | A1 | 7/2009 | Hon |
| 2009/0230117 | A1 | 9/2009 | Fernando et al. |
| 2009/0272379 | A1 | 11/2009 | Thorens et al. |
| 2009/0283103 | A1 | 11/2009 | Nielsen et al. |
| 2009/0320863 | A1 | 12/2009 | Fernando et al. |
| 2010/0043809 | A1 | 2/2010 | Magnon |
| 2010/0083959 | A1 | 4/2010 | Siller |
| 2010/0200006 | A1 | 8/2010 | Robinson et al. |
| 2010/0229881 | A1 | 9/2010 | Hearn |
| 2010/0242974 | A1 | 9/2010 | Pan |
| 2010/0307518 | A1 | 12/2010 | Wang |
| 2010/0313901 | A1 | 12/2010 | Fernando et al. |
| 2011/0005535 | A1 | 1/2011 | Xiu |
| 2011/0011396 | A1 | 1/2011 | Fang |
| 2011/0036363 | A1 | 2/2011 | Urtsev et al. |
| 2011/0036365 | A1 | 2/2011 | Chong et al. |
| 2011/0094523 | A1 | 4/2011 | Thorens et al. |
| 2011/0126848 | A1 | 6/2011 | Zuber et al. |
| 2011/0155153 | A1 | 6/2011 | Thorens et al. |
| 2011/0155718 | A1 | 6/2011 | Greim et al. |
| 2011/0168194 | A1 | 7/2011 | Hon |

(56) References Cited

U.S. PATENT DOCUMENTS

| | | |
|---|---|---|
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0255546 A1 | 10/2012 | Goetz et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0167854 A1 | 7/2013 | Shin |
| 2013/0192619 A1 | 8/2013 | Tucker et al. |
| 2013/0255702 A1 | 10/2013 | Griffith, Jr. et al. |
| 2013/0306084 A1 | 11/2013 | Flick |
| 2013/0312776 A1 | 11/2013 | Newton |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2013/0340778 A1 | 12/2013 | Liu |
| 2014/0000638 A1 | 1/2014 | Sebastian et al. |
| 2014/0014125 A1 | 1/2014 | Fernando et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0202454 A1 | 7/2014 | Buchberger |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2014/0353185 A1 | 12/2014 | Liu |
| 2015/0007838 A1 | 1/2015 | Fernando et al. |
| 2015/0034103 A1 | 2/2015 | Hon |
| 2015/0053217 A1 | 2/2015 | Steingmber et al. |
| 2015/0101625 A1 | 4/2015 | Newton et al. |
| 2015/0181942 A1 | 7/2015 | Holzherr et al. |
| 2015/0245654 A1 | 9/2015 | Memari et al. |
| 2015/0245655 A1 | 9/2015 | Memari et al. |
| 2015/0245656 A1 | 9/2015 | Memari et al. |
| 2015/0245662 A1 | 9/2015 | Memari et al. |
| 2015/0245663 A1 | 9/2015 | Memari et al. |
| 2015/0245664 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2016/0037826 A1 | 2/2016 | Hearn et al. |
| 2016/0150824 A1 | 6/2016 | Memari et al. |
| 2016/0262459 A1 | 9/2016 | Monsees et al. |
| 2016/0302488 A1 | 10/2016 | Fernando et al. |
| 2016/0366946 A1 | 12/2016 | Murison et al. |

FOREIGN PATENT DOCUMENTS

| | | |
|---|---|---|
| CA | 2 947 135 | 11/2015 |
| CN | 2437632 | 7/2001 |
| CN | 1541577 | 11/2004 |
| CN | 2719043 | 8/2005 |
| CN | 2839165 | 11/2006 |
| CN | 2872875 | 2/2007 |
| CN | 200997909 | 1/2008 |
| CN | 101116542 | 2/2008 |
| CN | 101176805 | 5/2008 |
| CN | 201379072 | 1/2010 |
| CN | 102835737 | 12/2012 |
| CN | 203087527 | 7/2013 |
| CN | 103989251 | 8/2014 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2903245 | 8/2015 |
| GB | 2469850 | 11/2010 |
| KR | 10-2015-0071150 | 6/2015 |
| RU | 132318 | 9/2013 |
| WO | WO 1997/48293 | 12/1997 |
| WO | WO 00/18458 | 4/2000 |
| WO | WO 2002/47499 | 6/2002 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2012/114322 | 8/2012 |
| WO | WO 2013/012157 | 1/2013 |
| WO | WO 2013/083636 | 6/2013 |
| WO | WO 2013/089551 | 6/2013 |
| WO | WO 2013/102612 | 7/2013 |
| WO | WO 2014/195679 | 12/2014 |
| WO | WO 2014/195687 | 12/2014 |
| WO | WO 2014/195688 | 12/2014 |
| WO | WO 2015/066136 | 5/2015 |
| WO | WO 2015/140555 | 9/2015 |
| WO | WO 2015/149332 | 10/2015 |
| WO | WO 2015/168588 | 11/2015 |
| WO | WO 2016/028544 | 2/2016 |
| WO | WO 2016/099045 | 6/2016 |
| WO | WO 2017/153951 | 9/2017 |

OTHER PUBLICATIONS

Richard Halliday; *Key Benefits of Next-Gen UV LED Technology*, Lumex® (4 pages). Downloaded from website on Aug. 21, 2014. http://www.digikey.com/Web%20Export/Supplier%20Content/Lumex_67/PDF/Lumex_UV_LEDs_TechNotes.pdf?redirected=1.

Olga Bilenko et al.; SETi Sensor Electronic Technology, Inc.; *Water Sterilization Using Semiconductor-Based Deep Ultraviolet Light Sources* (2 pages). Downloaded from website on Aug. 21, 2014. http://www.s-et.com/water-sterilization-using-uv-leds.pdf.

GB1408173.1 priority document for Memari, May 8, 2014.

VQASE, Jul. 27, 2014, www.vqase.com [downloaded online from archive.org on Dec. 22, 2016].

Steve K, Jun. 3, 2016, E-zip-www.steveape.com [downloaded online from archive.org on Dec. 22, 2016].

AEROSOL DELIVERY DEVICE INCLUDING A MOVEABLE CARTRIDGE AND RELATED ASSEMBLY METHOD

CROSS-REFERENCE TO RELATED APPLICATIONS

This application is a continuation of U.S. application Ser. No. 15/882,744, filed Jan. 29, 2018, which is a continuation of U.S. application Ser. No. 14/465,167, filed Aug. 21, 2014, each of which being hereby incorporated by reference in its entirety in this application.

FIELD OF THE DISCLOSURE

The present disclosure relates to aerosol delivery devices, and more particularly, to aerosol delivery devices that include a cartridge moveable between multiple configurations relative to a separate housing. The aerosol delivery device includes an atomizer comprising a heating element configured to heat an aerosol precursor. The aerosol precursor composition, which may include components made or derived from tobacco or otherwise incorporate tobacco, is heated by the atomizer to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0060554 to Collett et al., U.S. Pat. App. Pub. No. 2014/0096781 to Sears et al., U.S. patent application Ser. No. 13/826,929 to Ampolini et al., filed Mar. 14, 2013, and U.S. patent application Ser. No. 14/011,992 to Davis et al., filed Aug. 28, 2013, which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et. al, which are incorporated by reference in their entireties.

Certain existing embodiments of aerosol delivery devices include a control body and a cartridge. A power source (e.g., a battery) may be positioned in the control body and an aerosol precursor composition may be positioned in the cartridge. The cartridge and the control body may engage one another to define an elongated tubular configuration. However, certain other form factors for aerosol delivery devices may be desirable.

BRIEF SUMMARY OF THE DISCLOSURE

The present disclosure relates to aerosol delivery devices which, in certain embodiments, may be characterized as electronic cigarettes.

In one aspect an aerosol delivery device is provided. The aerosol delivery device may include an atomizer, a reservoir configured to contain an aerosol precursor composition, a housing, and a cartridge comprising a mouthpiece. The housing may also be referred to as a control body, and the cartridge may be releasably coupled to the housing in some embodiments. The cartridge may be moveable relative to at least a portion of the housing between an extended configuration in which the mouthpiece is exposed and a retracted configuration in which the mouthpiece is relatively closer to the housing than in the extended configuration.

In some embodiments the cartridge may include the reservoir. Further, the cartridge may include the atomizer. The cartridge may be replaceable. The aerosol delivery device may additionally include an actuator coupled to the cartridge and configured to move the cartridge between the extended configuration and the retracted configuration.

In some embodiments the actuator may include a slider. The slider may be configured to cover an opening defined in the housing when the cartridge is in the retracted configuration such that the cartridge is substantially enclosed in the housing and further configured to retract from at least a portion of the opening to allow the cartridge to extend through the opening in the extended configuration. The actuator may include a spring and a button. The spring may be configured to move the cartridge from the retracted configuration to the extended configuration upon actuation of the button.

The housing may include a moveable portion pivotably connected to a main body portion. The actuator may include a connecting mechanism configured to move the cartridge from the retracted configuration to the extended configuration during opening of the moveable portion and configured to move the cartridge from the extended configuration to the retracted configuration during closing of the moveable portion. The cartridge may be configured to pivot with respect to the housing. The cartridge may be configured to remain stationary with respect to a main body portion of the housing. The mouthpiece may be positioned inside the housing in the retracted configuration.

In an additional aspect a method for assembling an aerosol delivery device is provided. The method may include providing an atomizer, a reservoir configured to contain an aerosol precursor composition, a housing, and a cartridge comprising a mouthpiece, positioning the atomizer in the cartridge or the housing, positioning the reservoir in the cartridge or the housing, and operatively engaging the cartridge with the housing such that the cartridge is moveable relative to at least a portion of the housing between an extended configuration in which the mouthpiece is exposed and a retracted configuration in which the mouthpiece is relatively closer to the housing than in the extended configuration.

In some embodiments positioning the reservoir in the cartridge or the housing may include positioning the reservoir in the cartridge. Positioning the atomizer in the cartridge or the housing may include positioning the atomizer in the cartridge. Operatively engaging the cartridge with the housing may include coupling the cartridge to an actuator. The actuator may be configured to move the cartridge between the extended configuration and the retracted configuration. Coupling the cartridge to the actuator may include inserting a slider at least partially within the housing. The slider may be configured to cover an opening in the housing in the retracted configuration such that the cartridge is substantially enclosed in the housing and further configured to retract from at least a portion of the opening to allow the cartridge to extend through the opening in the extended configuration. The method may additionally include pivotably coupling a main body portion of the housing to a moveable portion of the housing. Operatively engaging the cartridge with the housing may include pivotably coupling the cartridge to the housing.

In an additional aspect an aerosol delivery device is provided. The aerosol delivery device may include a housing, a connector comprising a coupler configured to engage a cartridge comprising atomizer and a reservoir containing an aerosol precursor composition, and an actuator at least partially received within the housing and engaged with the connector, the actuator being configured to move the cartridge relative to at least a portion of the housing between an extended configuration and a retracted configuration.

In some embodiments the aerosol delivery device may additionally include a power source. The aerosol delivery device may further include a controller. The controller may be configured to direct electrical power from the power source to the cartridge to heat the aerosol precursor composition retained in the reservoir with the atomizer to produce an aerosol. The actuator may include a slider configured to slide on a track. The actuator may additionally include an external engagement member configured for engagement by a user to move the slider.

In an additional aspect a method for assembling an aerosol delivery device is provided. The method may include providing a housing, an actuator, and a connector comprising a coupler configured to engage a cartridge comprising atomizer and a reservoir containing an aerosol precursor composition, coupling the connector to the actuator, and at least partially inserting the connector and the actuator within the housing such that the actuator is configured to move the cartridge relative to at least a portion of the housing between an extended configuration and a retracted configuration.

In some embodiments the method may additionally include inserting a power source into the housing. Further, the method may include inserting a controller into the housing. The controller may be configured to direct electrical power from the power source to the cartridge to heat the aerosol precursor composition retained in the reservoir with the atomizer to produce an aerosol. The method may additionally include assembling the actuator. Assembling the actuator may include engaging a slider with a track. Assembling the actuator may further include coupling an external engagement member to the slider. The external engagement member may be configured for engagement by a user to move the slider.

In an additional embodiment an aerosol delivery device is provided. The aerosol delivery device may include a housing, a power source within the housing, a connector moveably attached to the housing, and a cartridge comprising an outer body with a mouthpiece configured for passage of an aerosol therethrough. The cartridge may be engaged with the connector so as to be moveable relative to at least a portion of the housing.

In some embodiments the cartridge may include a reservoir configured to retain an aerosol precursor composition. The cartridge may include an atomizer. The cartridge may be removably engaged with the connector and replaceable.

In some embodiments the aerosol delivery device may additionally include an actuator coupled to the connector and configured to move the cartridge between an extended configuration in which the mouthpiece is exposed and a retracted configuration in which the mouthpiece is relatively closer to the housing than in the extended configuration. The actuator may include a slider. The slider may be configured to cover an opening defined in the housing when the cartridge is in the retracted configuration such that the cartridge is substantially enclosed in the housing and further configured to retract from at least a portion of the opening to allow the cartridge to extend through the opening in the extended configuration. The actuator may include a spring and a button. The spring may be configured to move the cartridge from the retracted configuration to the extended configuration upon actuation of the button.

In some embodiments the housing may include a moveable portion pivotably connected to a main body portion. The actuator may include a connecting mechanism configured to move the cartridge from the retracted configuration to the extended configuration during opening of the moveable portion and configured to move the cartridge from the extended configuration to the retracted configuration during closing of the moveable portion. The cartridge may be configured to pivot with respect to the housing. The mouthpiece may be positioned inside the housing in the retracted configuration.

In an additional embodiment an aerosol delivery device is provided. The aerosol delivery device may include a cartridge including an outer body with a mouthpiece configured for passage of an aerosol therethrough, a housing including a main body portion and a moveable portion, and a power source within the housing. The moveable portion of the housing may be configured to move with respect to the main body portion of the housing between a first position in which the mouthpiece of the cartridge is exposed and a second position in which the mouthpiece is at least partially received within the moveable portion of the housing.

In some embodiments the cartridge may be configured to remain stationary with respect to the main body portion of the housing. The moveable portion of the housing may be configured to translate toward and away from the main body portion of the housing. The moveable portion of the housing may be configured to pivot with respect to the main body portion of the housing.

In some embodiments the aerosol delivery device may further include a connector attached to the housing and engaged with the cartridge. The connector may be fixedly attached to the main body portion of the housing. The cartridge may be removably engaged with the connector and replaceable. The cartridge may include an atomizer.

In an additional embodiment a method for assembling an aerosol delivery device is provided. The method may include providing a housing, a power source, and a connector configured to engage a cartridge comprising an outer body with a mouthpiece configured for passage of an aerosol therethrough. The method may additionally include positioning the power source within the housing and moveably attaching the connector to the housing such that the connector is configured to move the cartridge relative to at least a portion of the housing.

In some embodiments the method may additionally include engaging the cartridge with the connector. The method may further include coupling the connector to an actuator. The actuator may be configured to move the cartridge between an extended configuration and a retracted configuration. Additionally, the method may include assembling the actuator. Assembling the actuator may include engaging a slider with a track. Assembling the actuator may additionally include coupling an external engagement member to the slider. The external engagement member may be configured for engagement by a user to move the slider.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
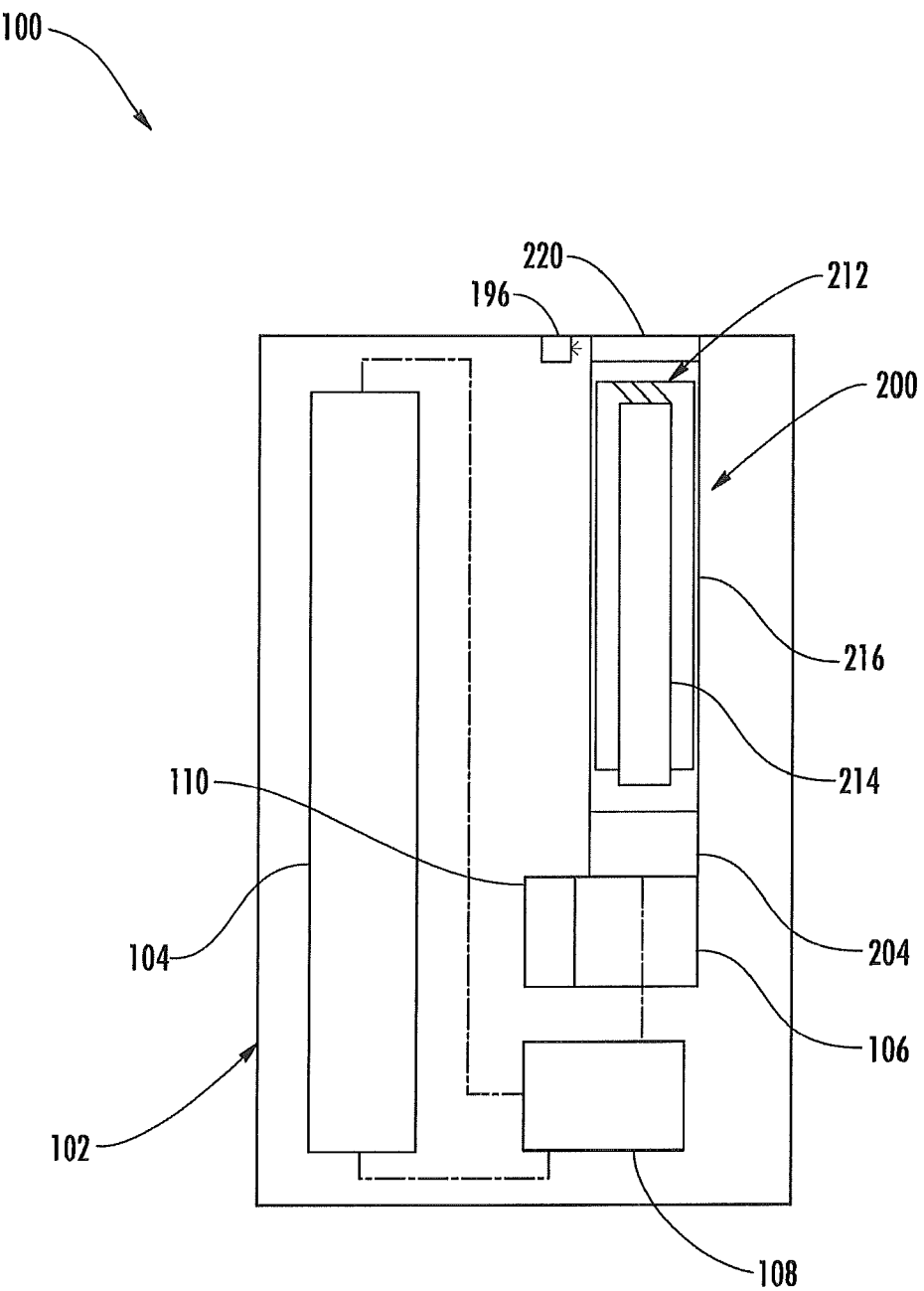
Figure 2:
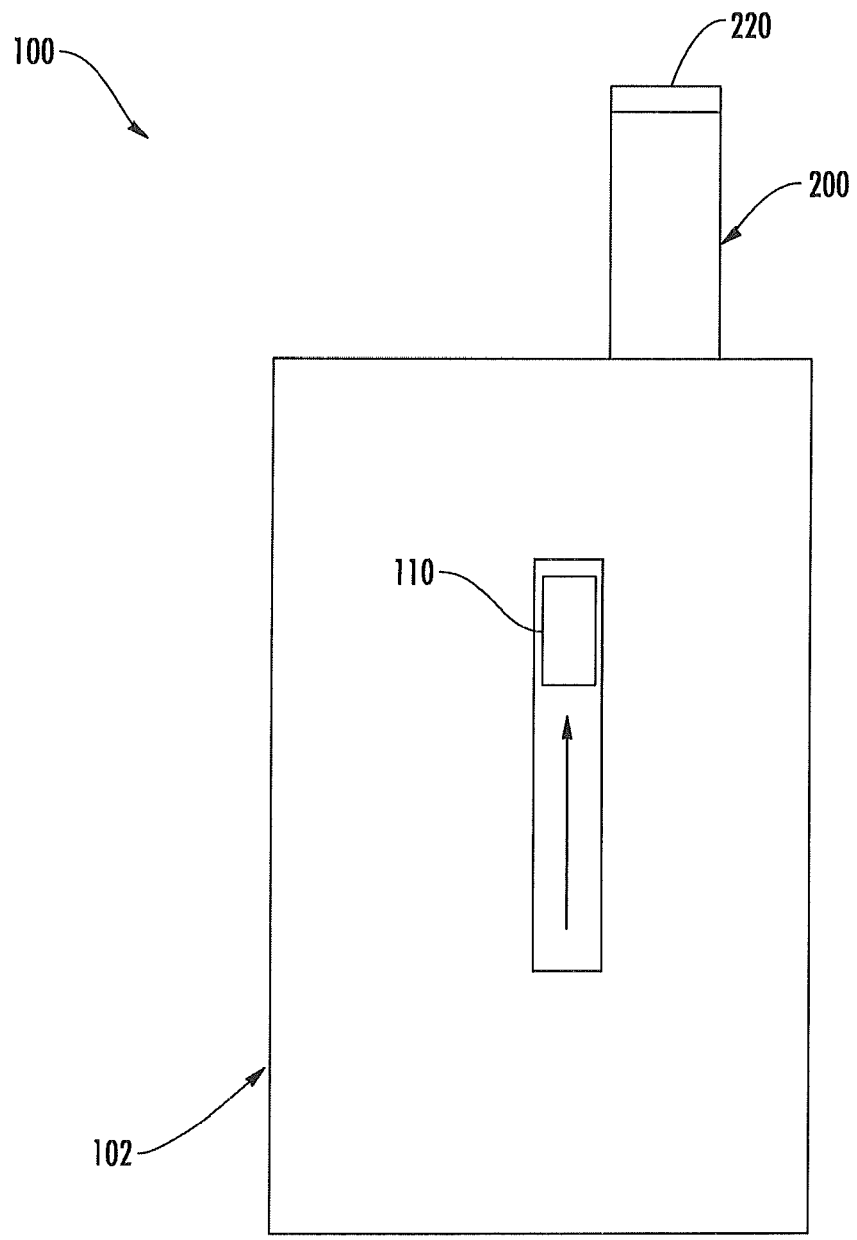
Figure 3:
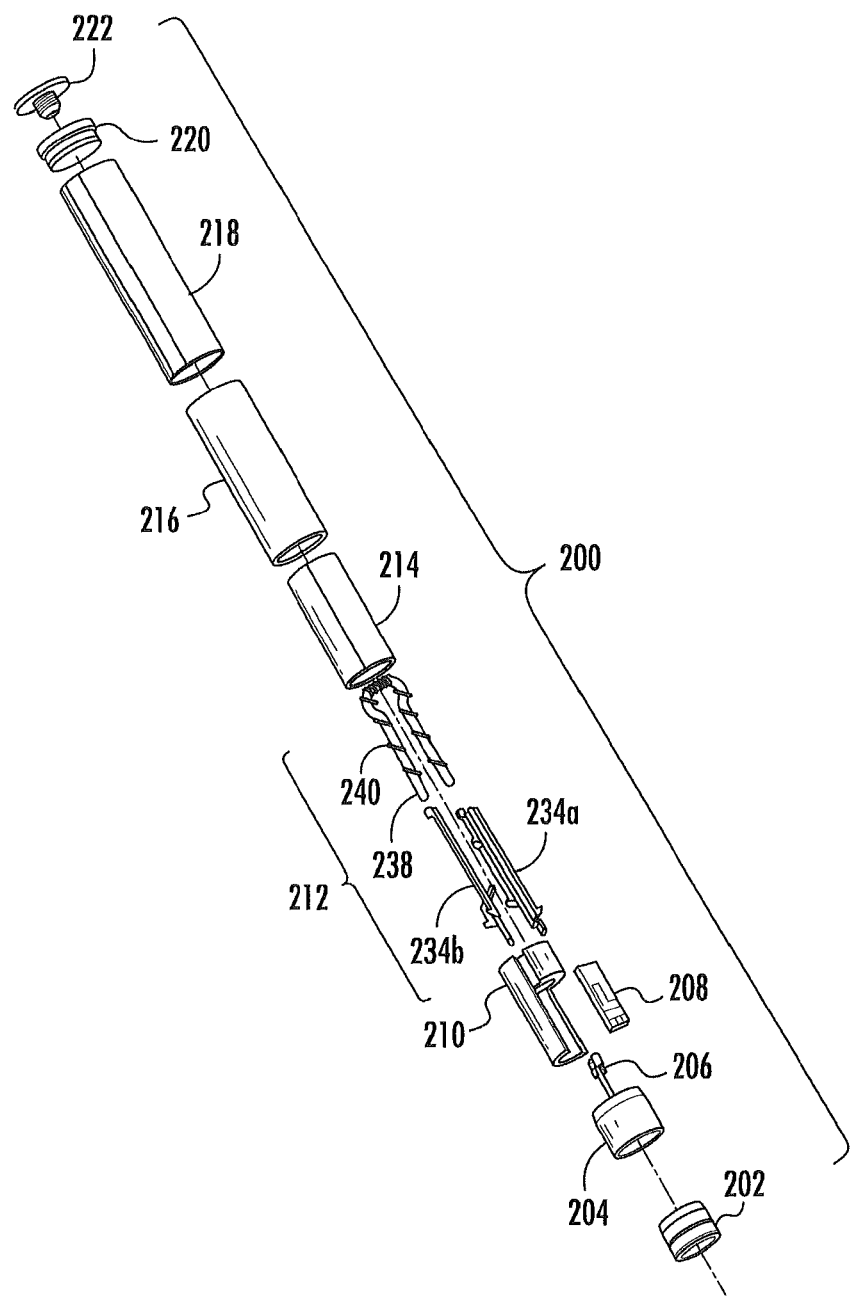
Figure 4:
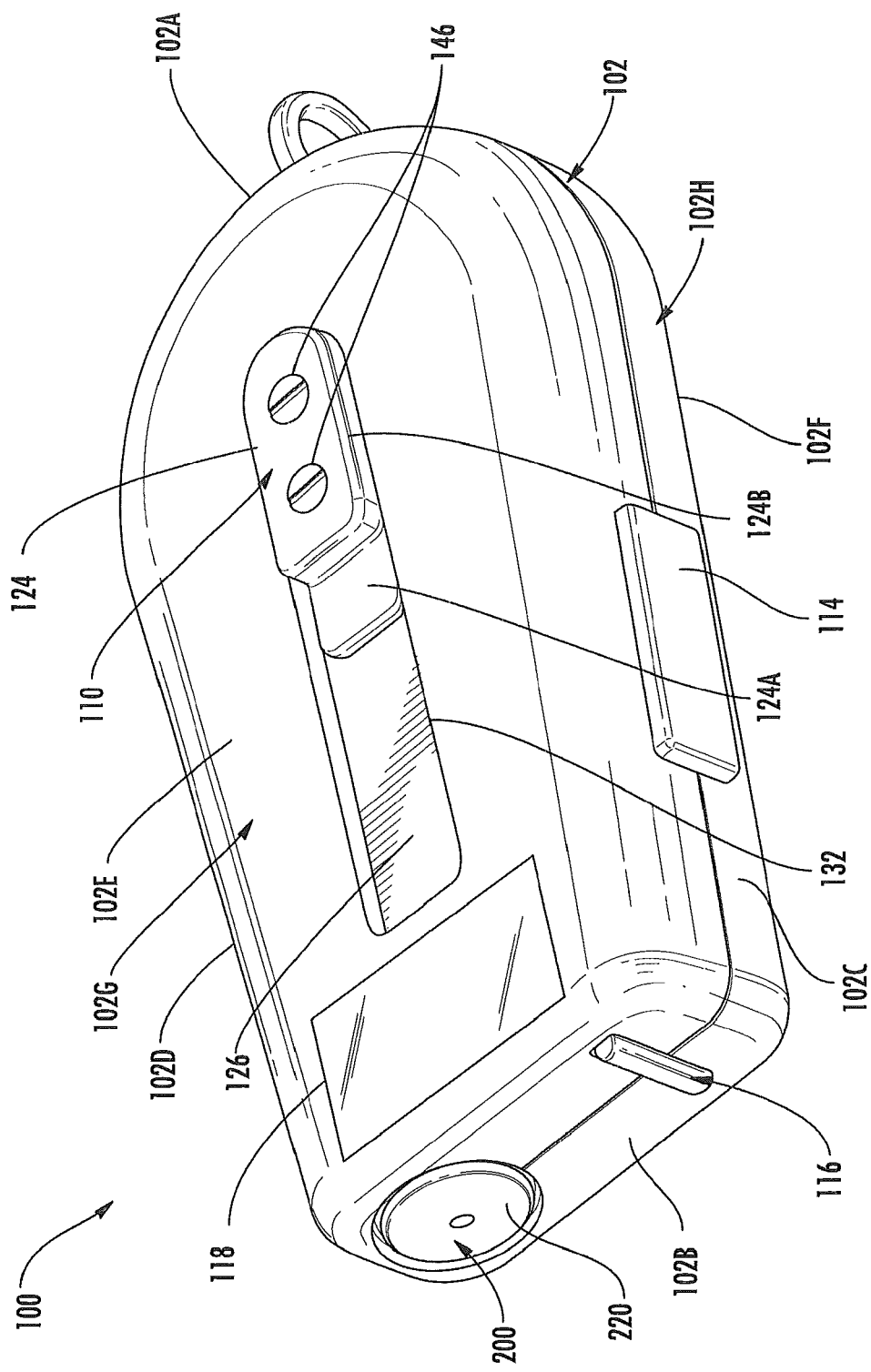
Figure 5:
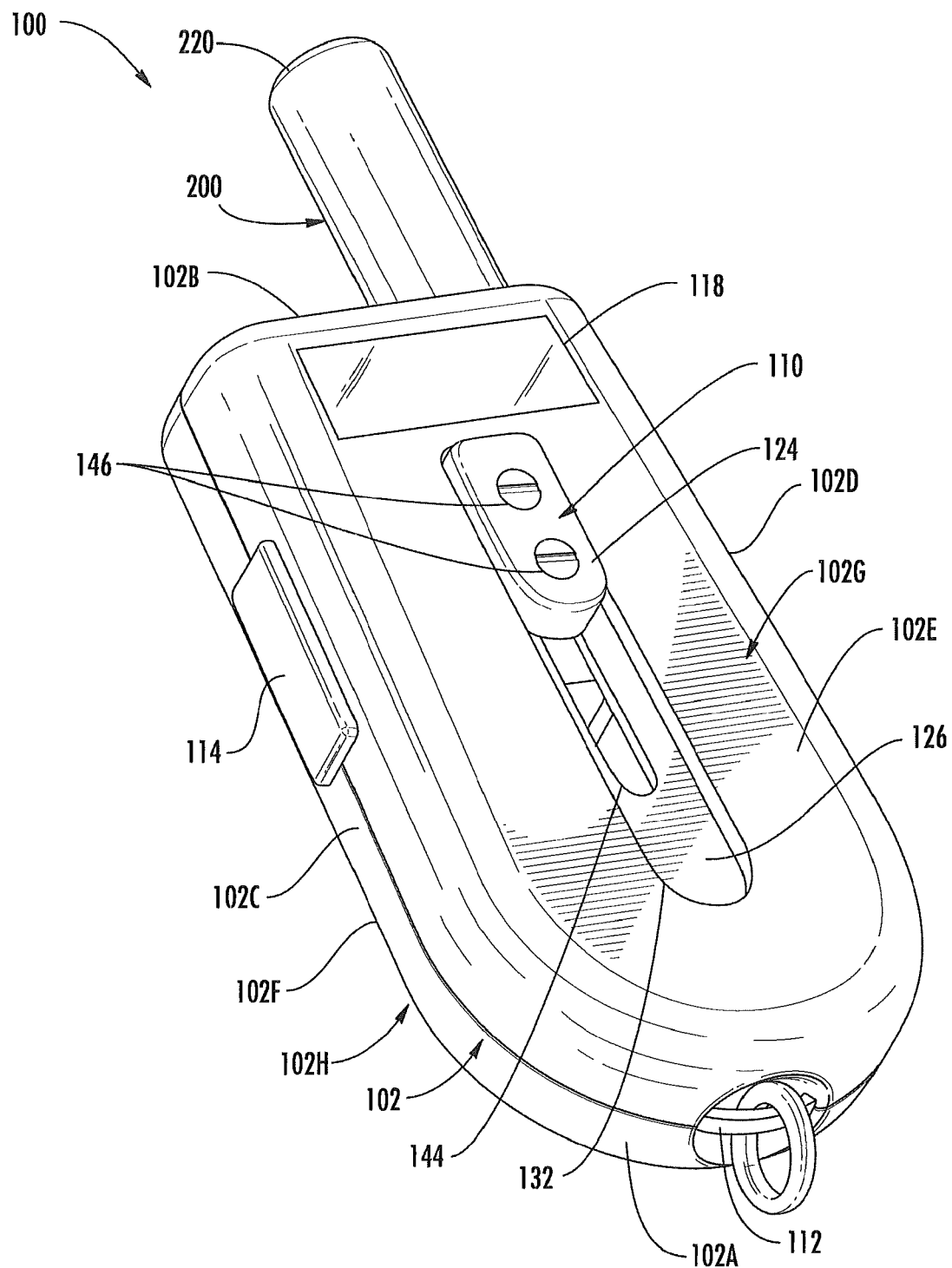
Figure 6:
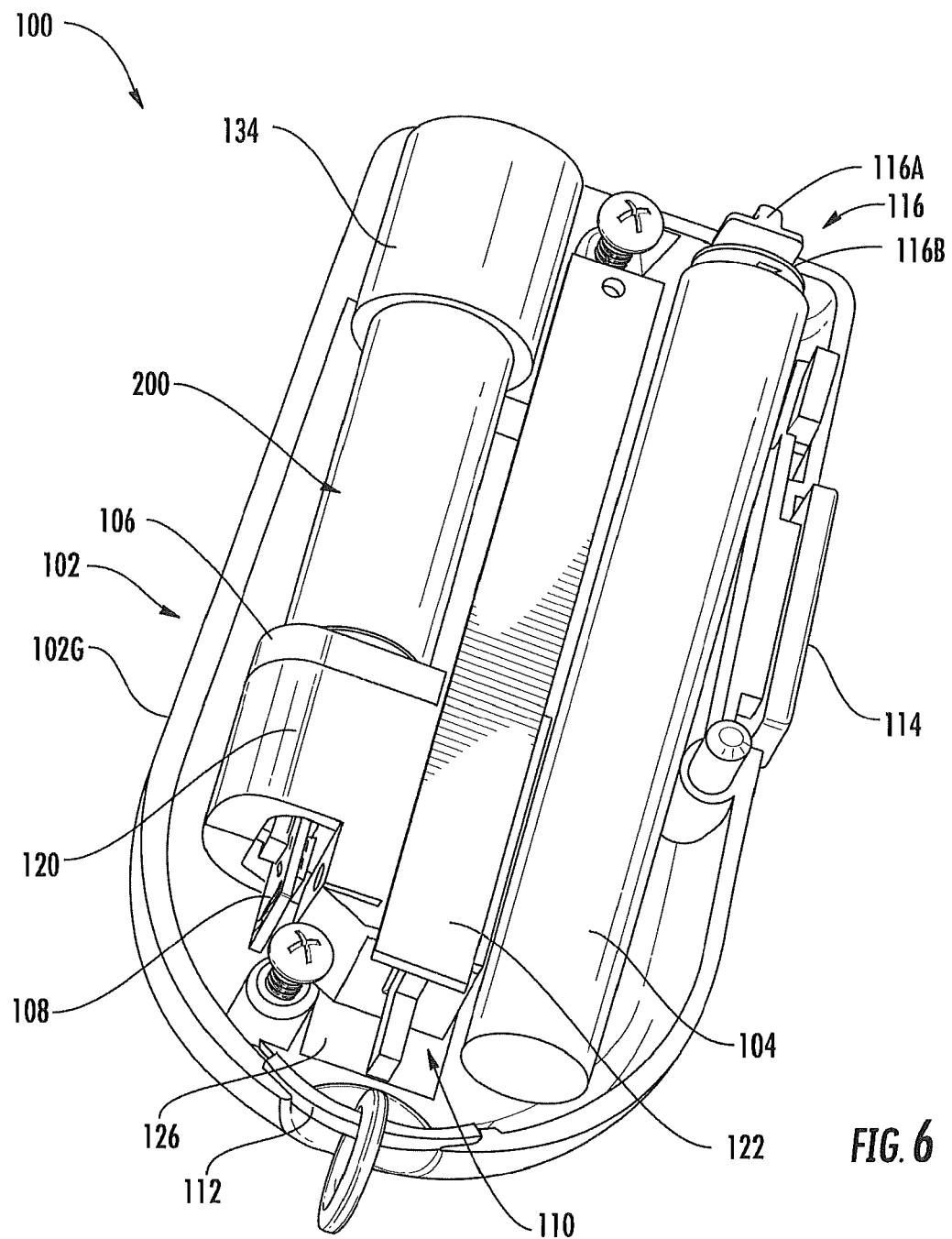
Figure 7:
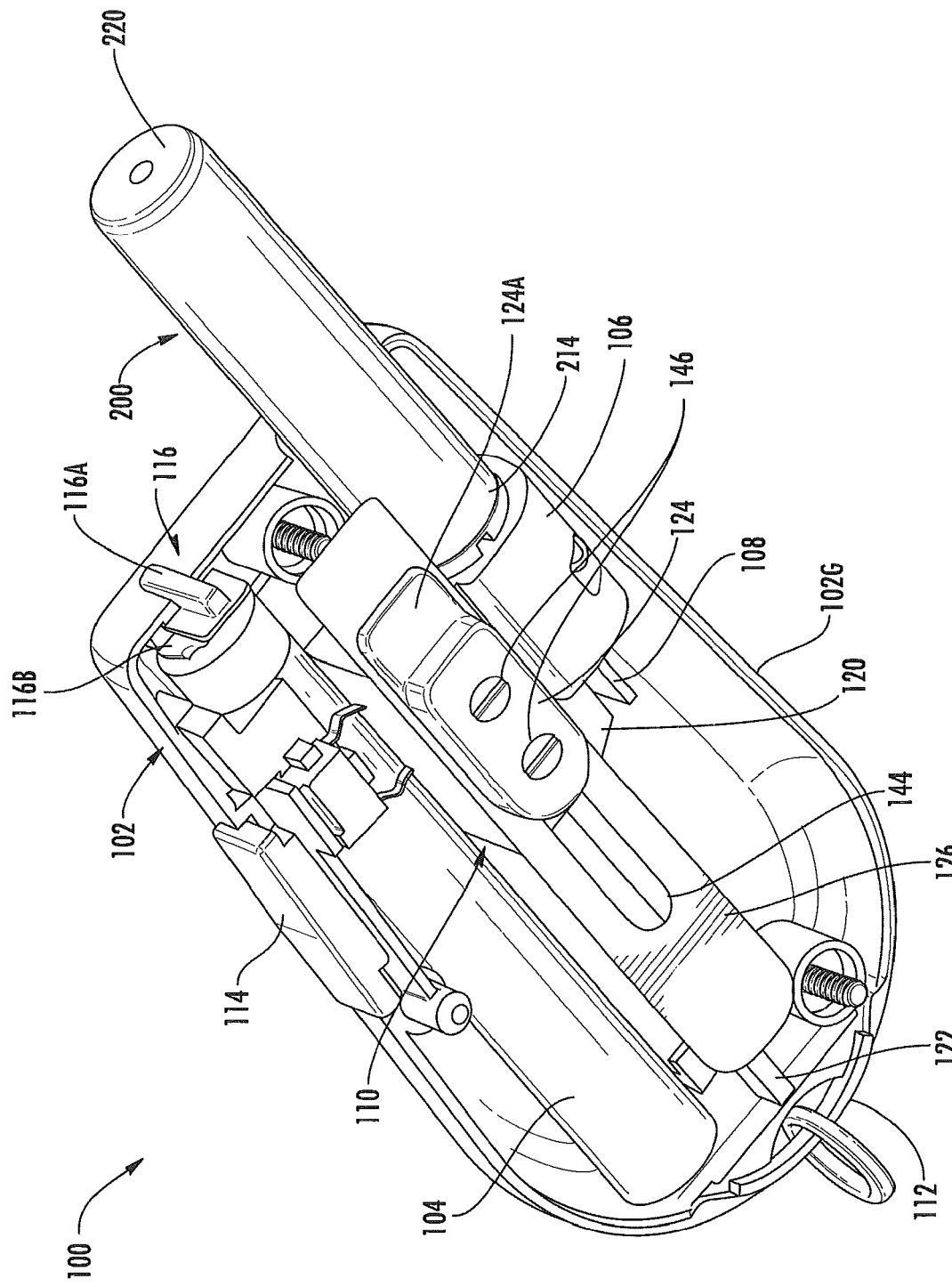
Figure 8:
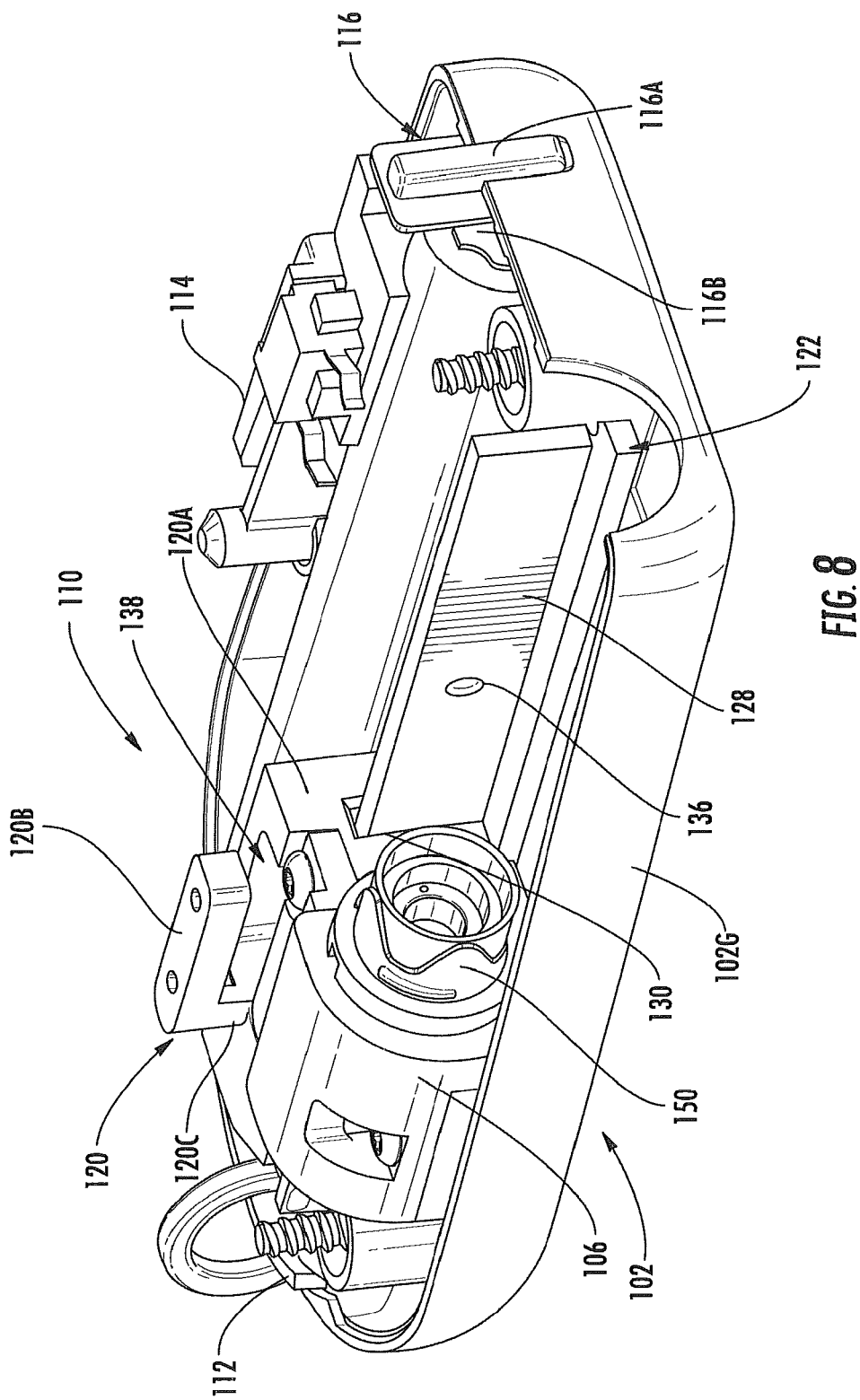
Figure 9:
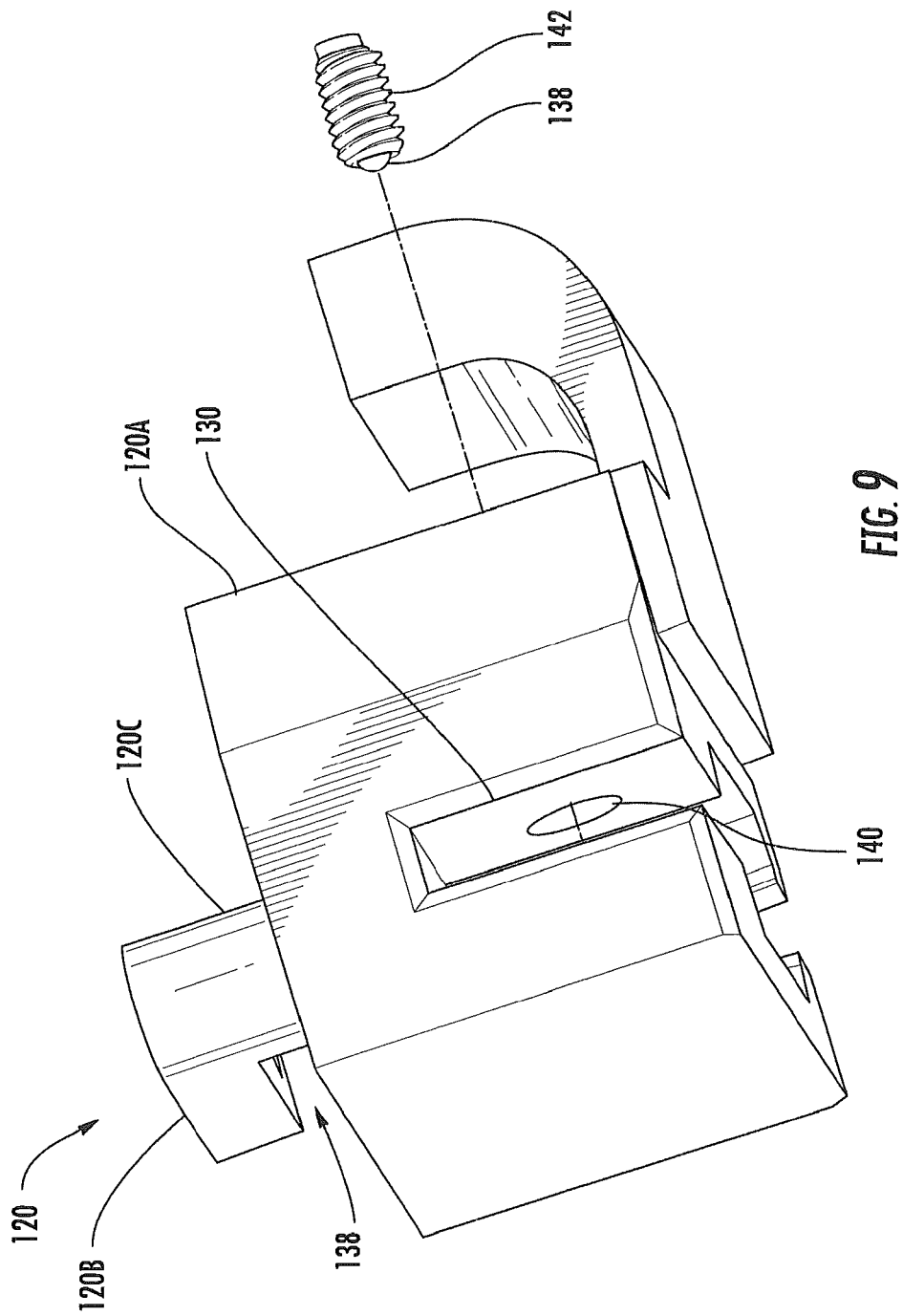
Figure 10:
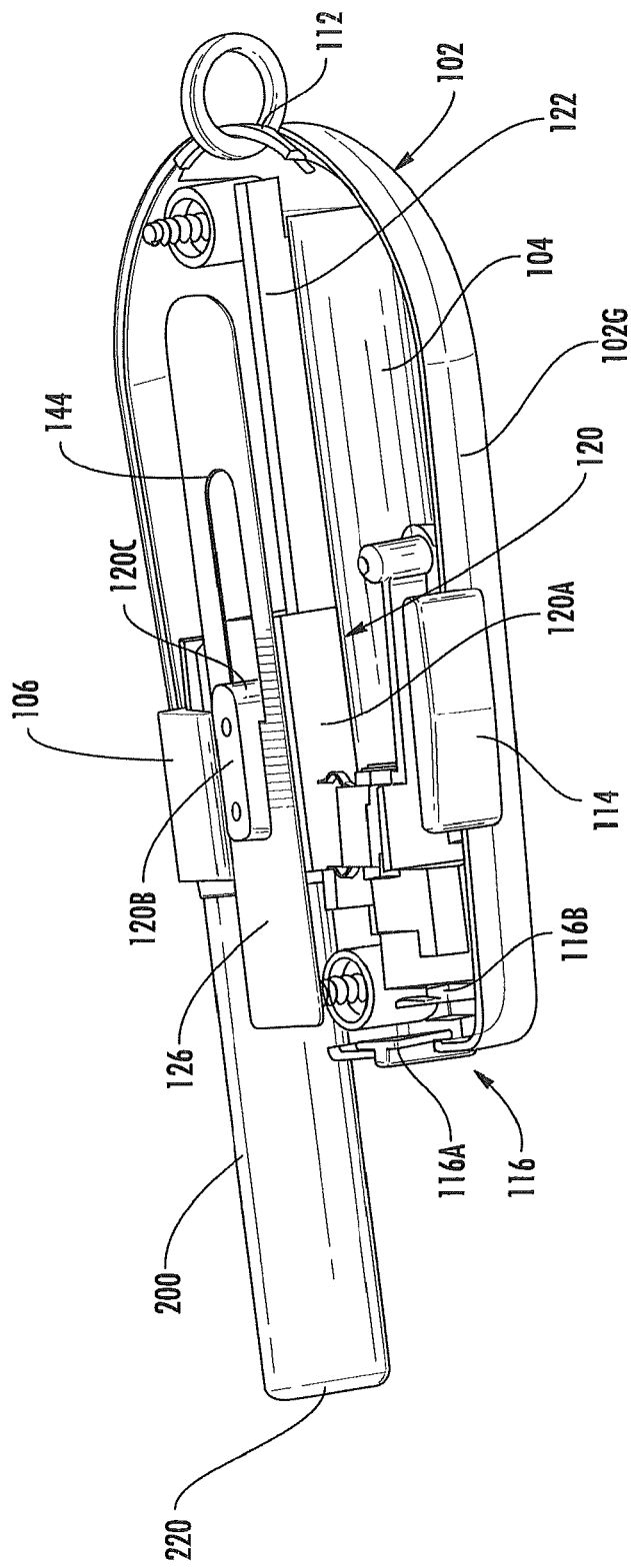
Figure 11:
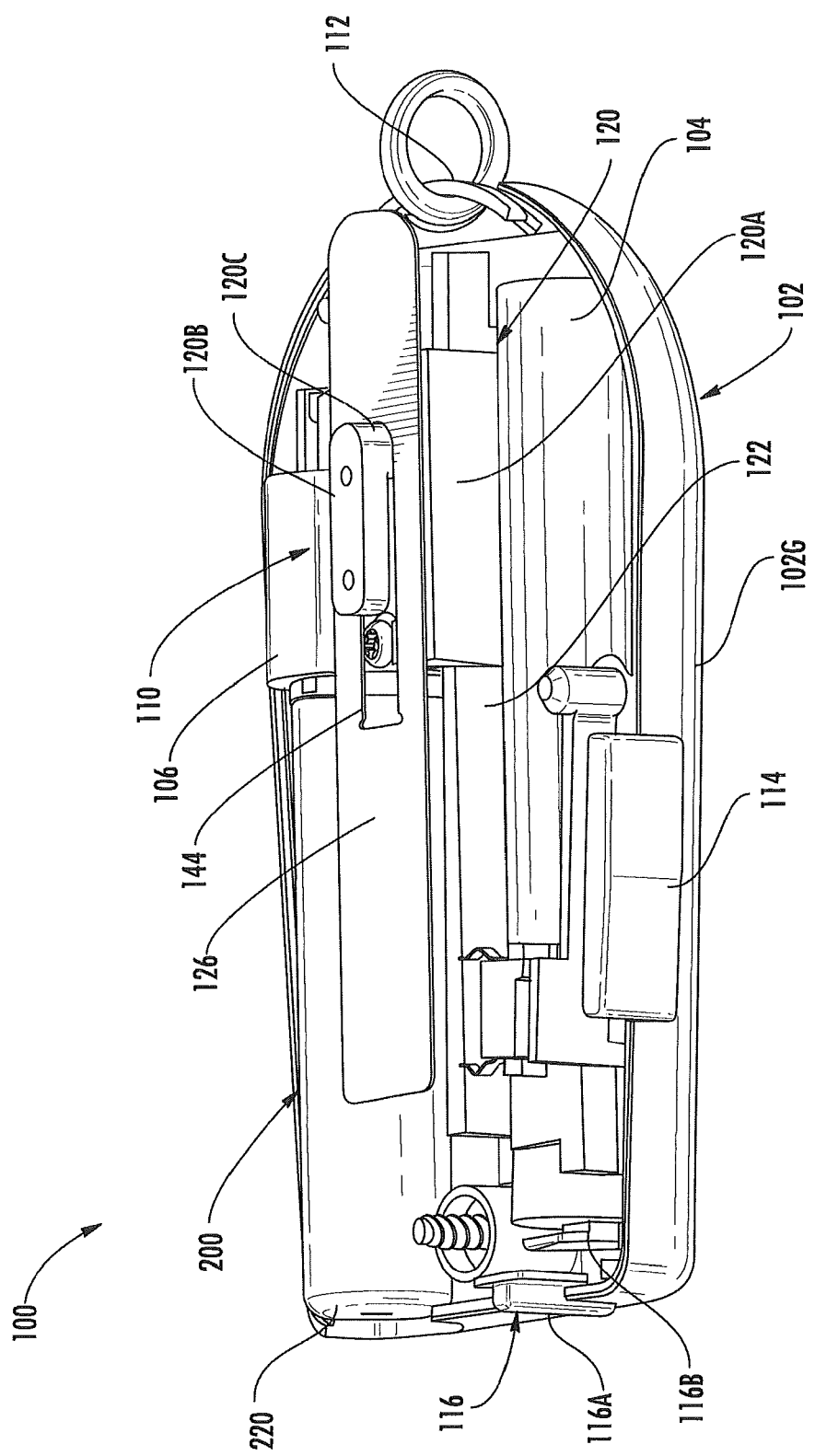
Figure 12:
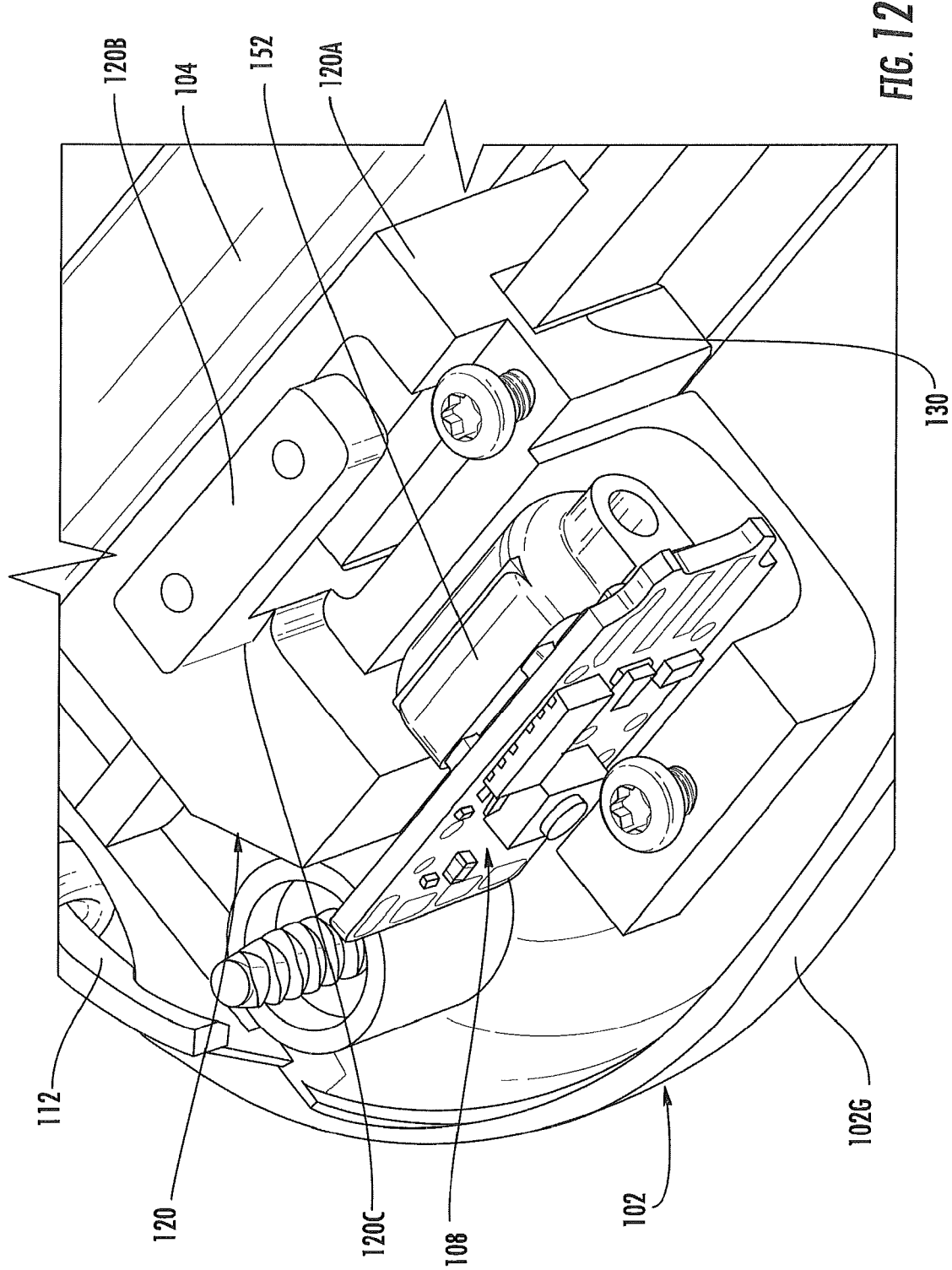
Figure 13:
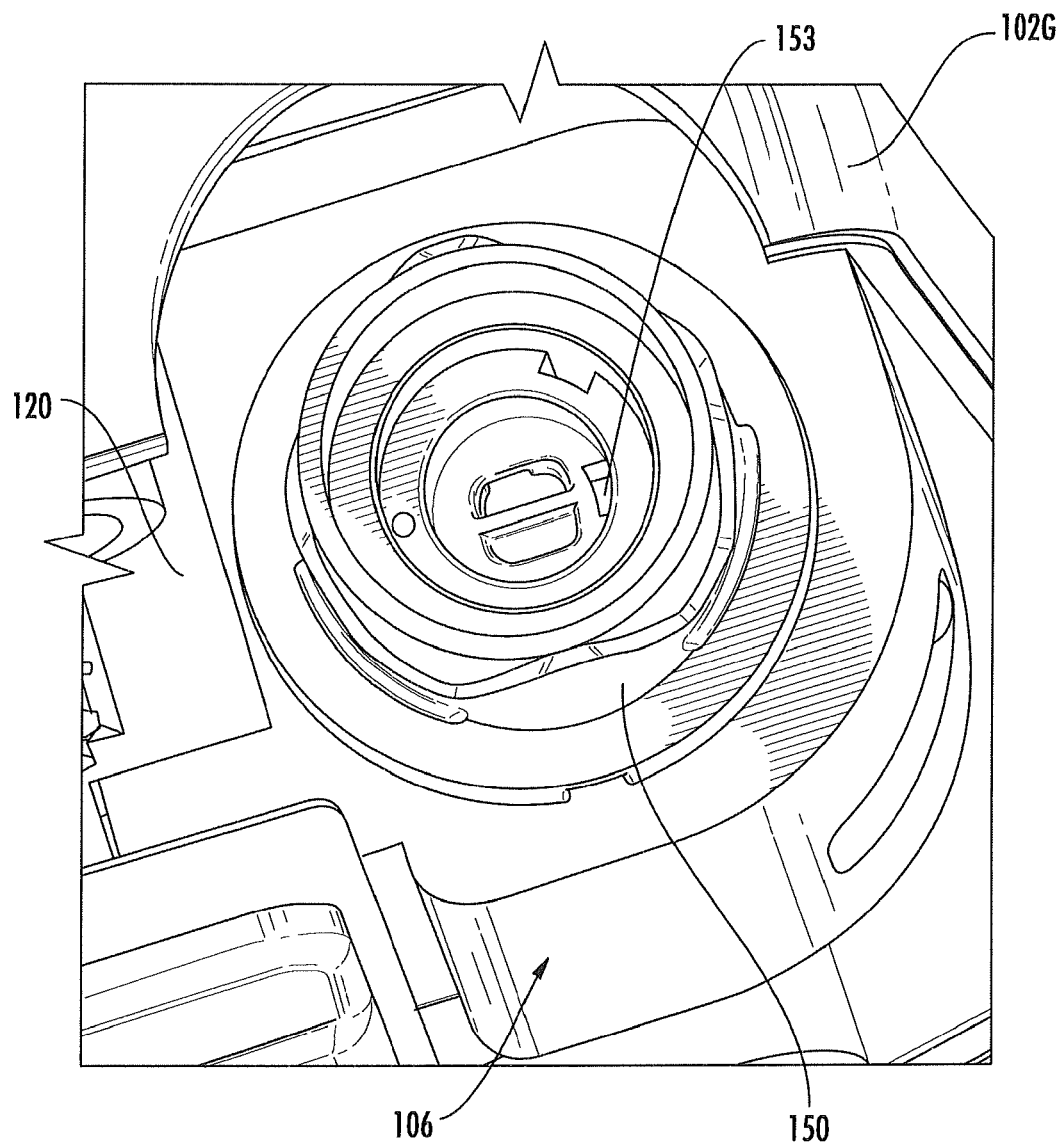
Figure 14:
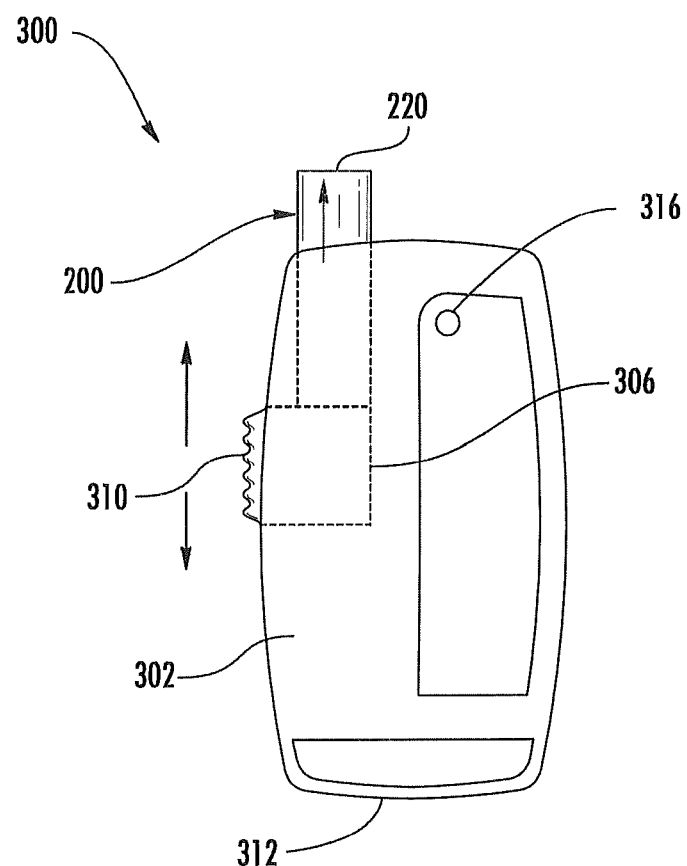
Figure 15:
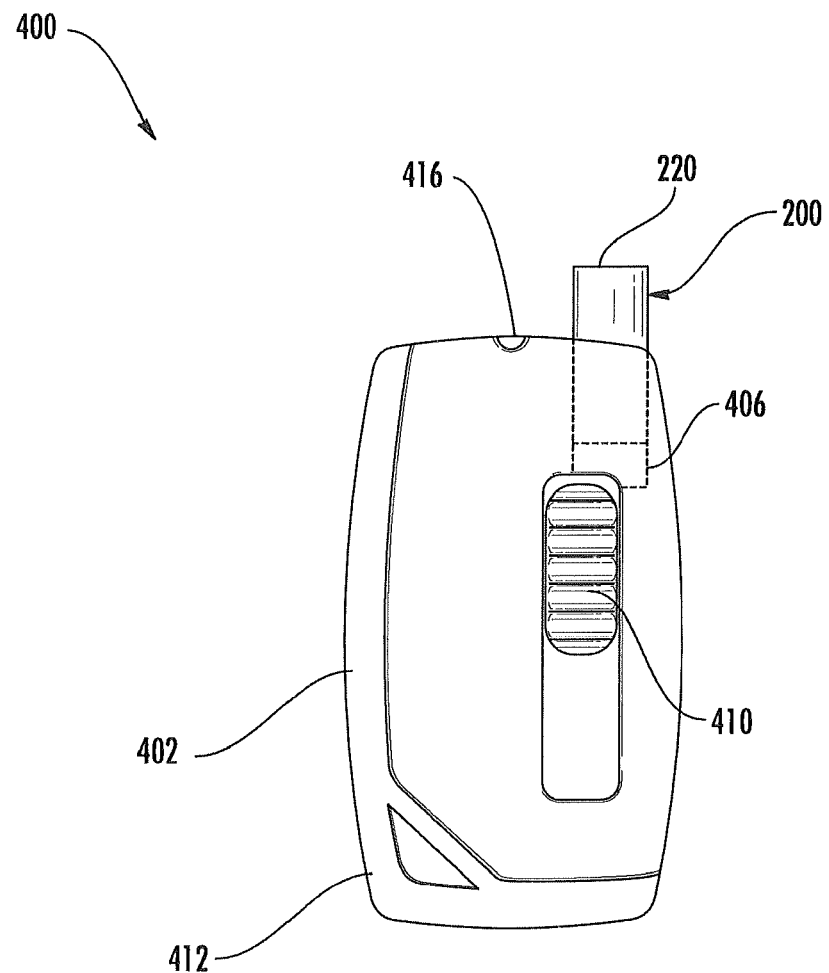
Figure 16:
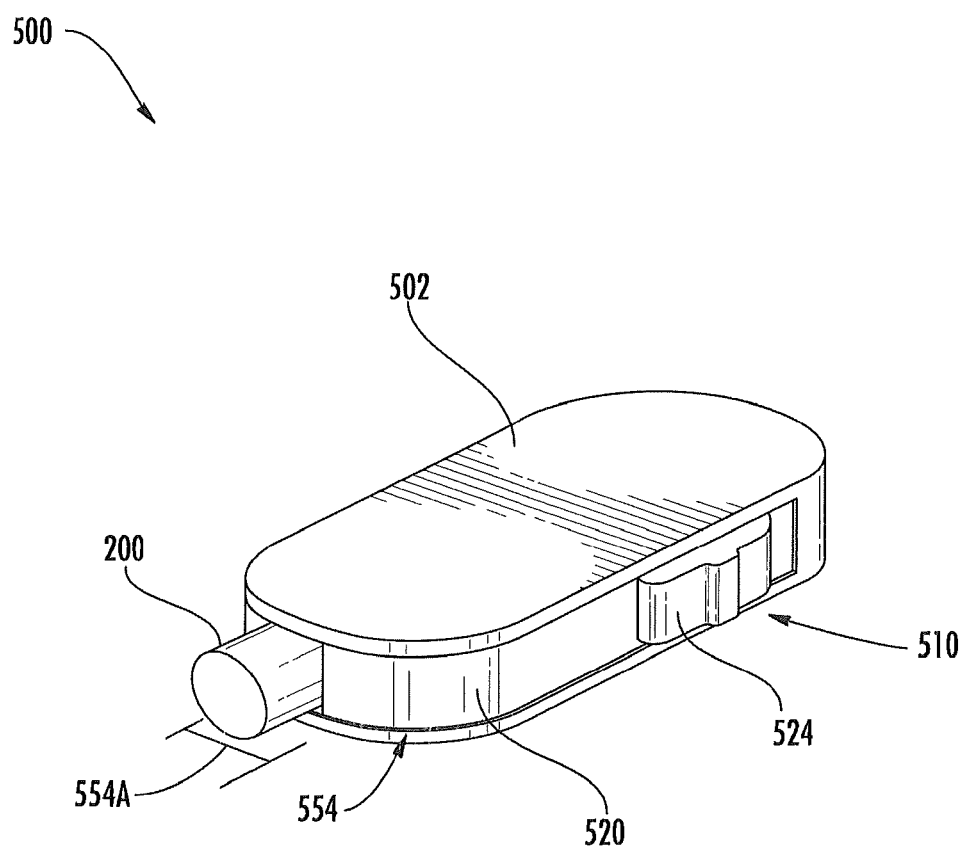
Figure 17:
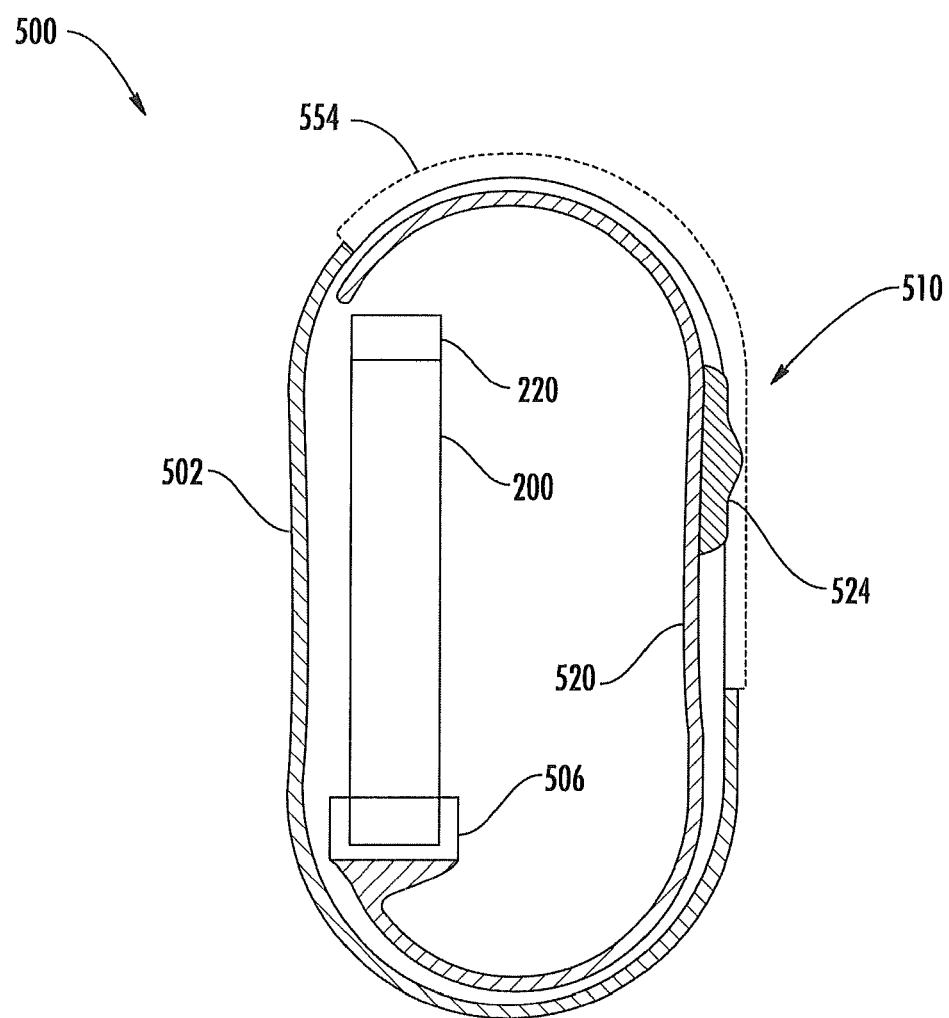
Figure 18:
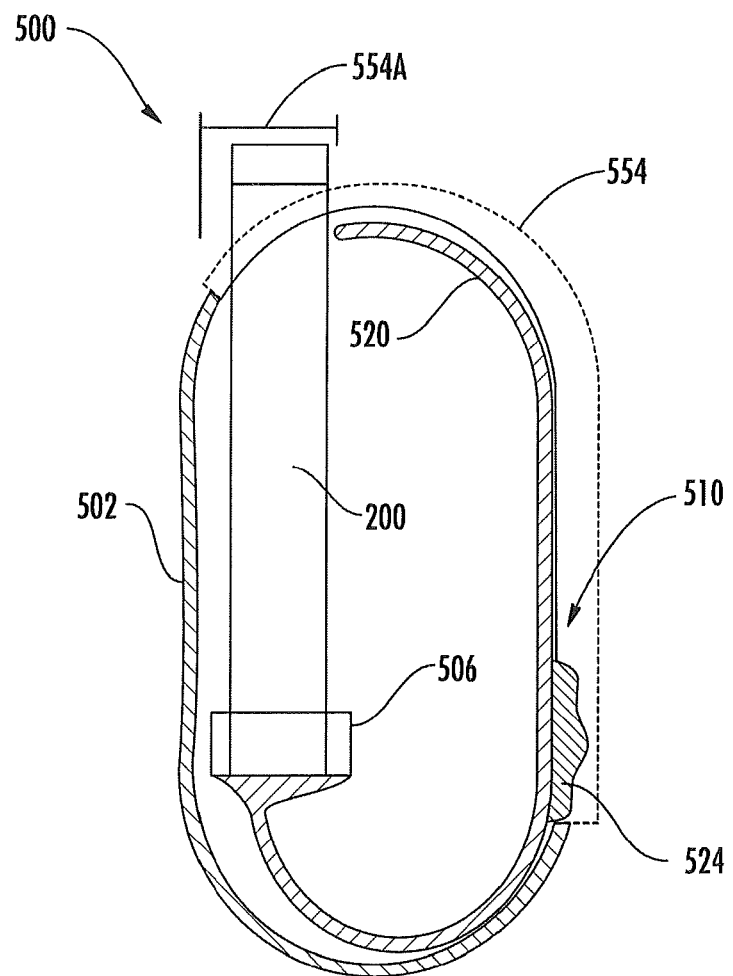
Figure 19:
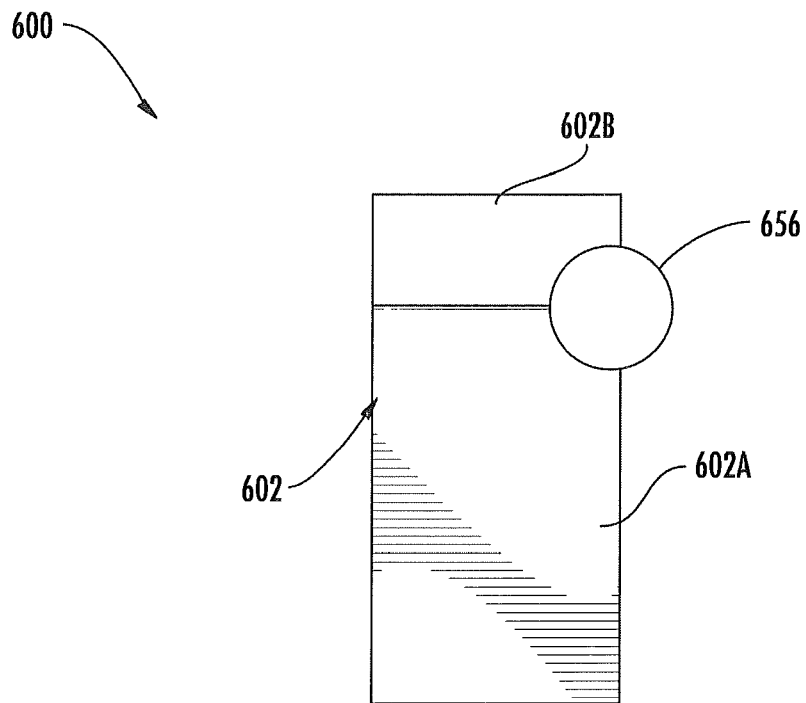
Figure 20:
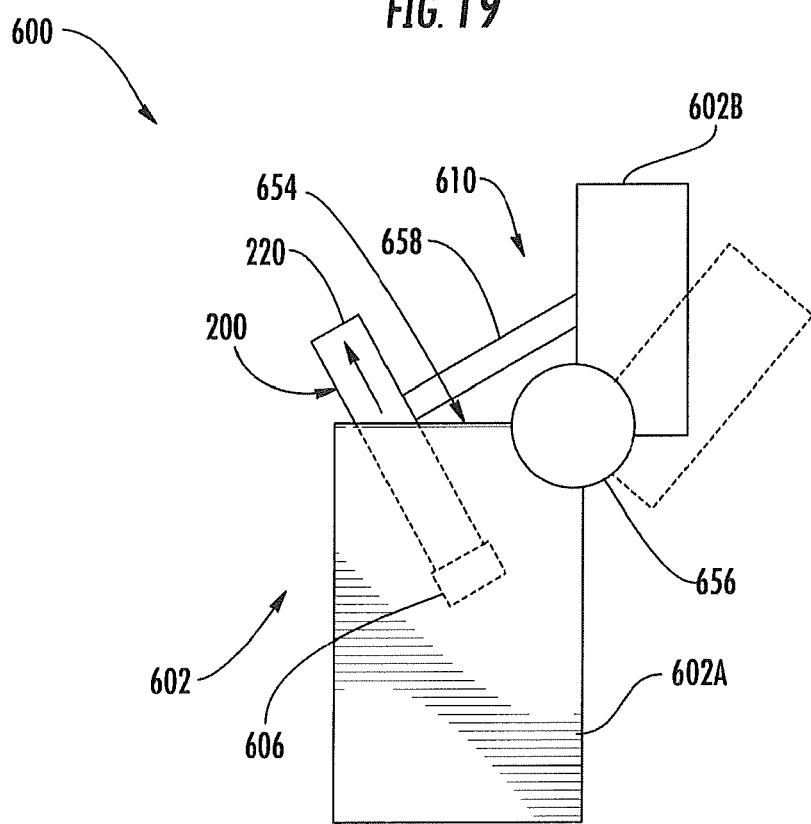
Figure 21:
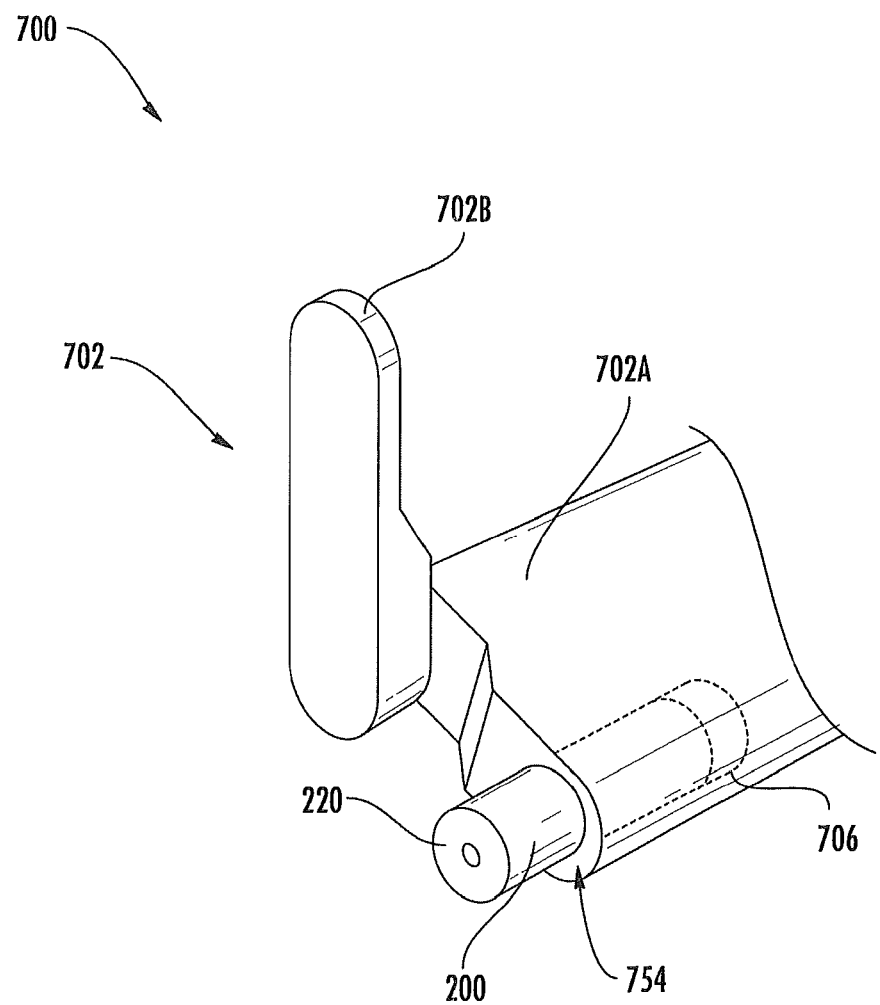
Figure 22:
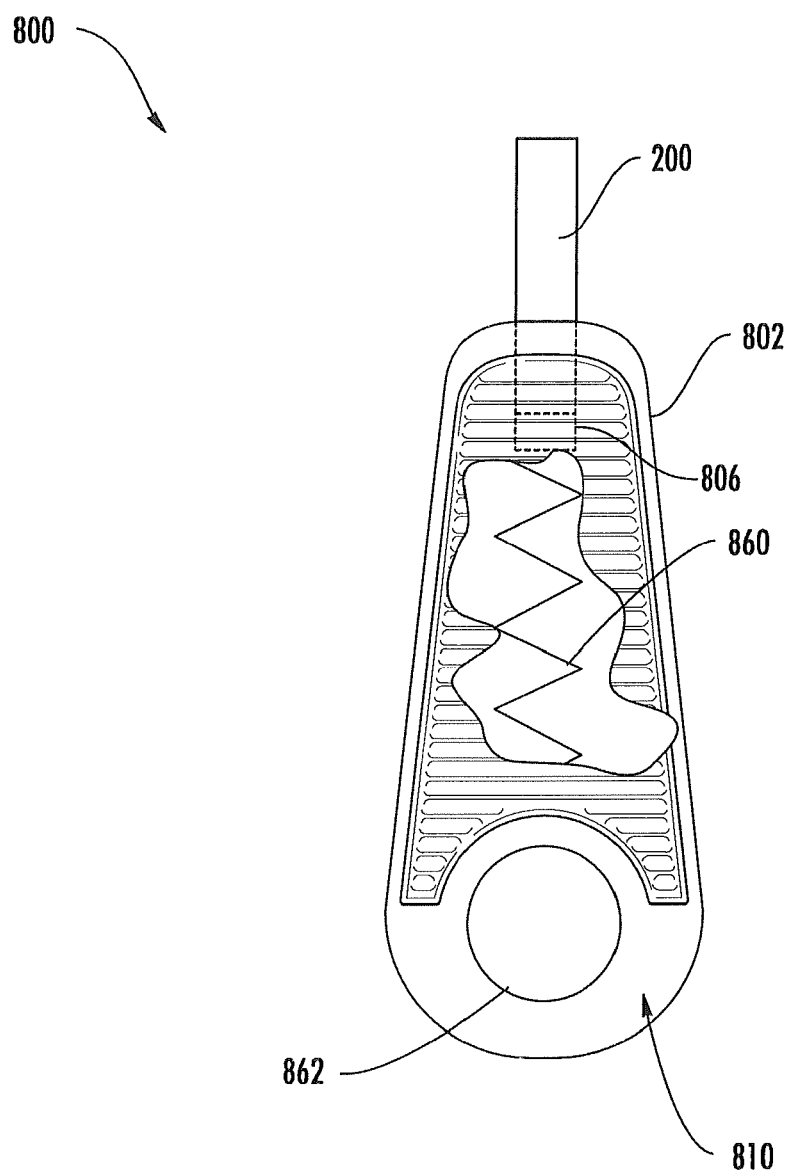
Figure 23:
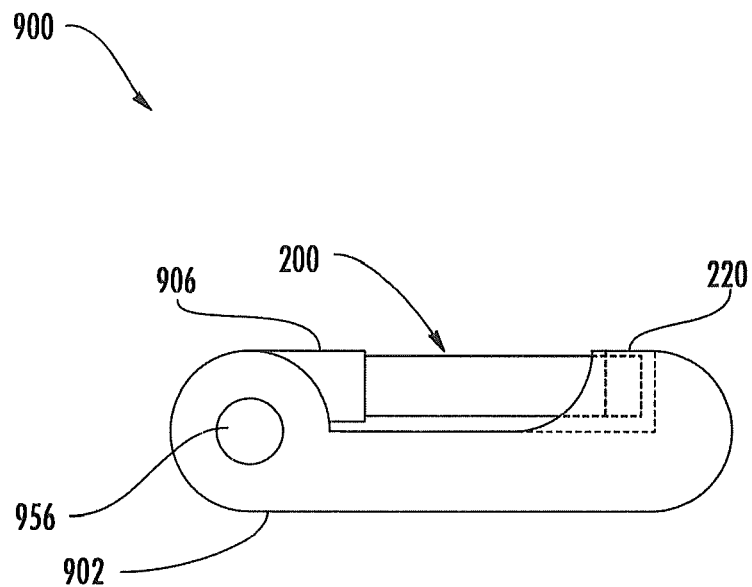
Figure 24:
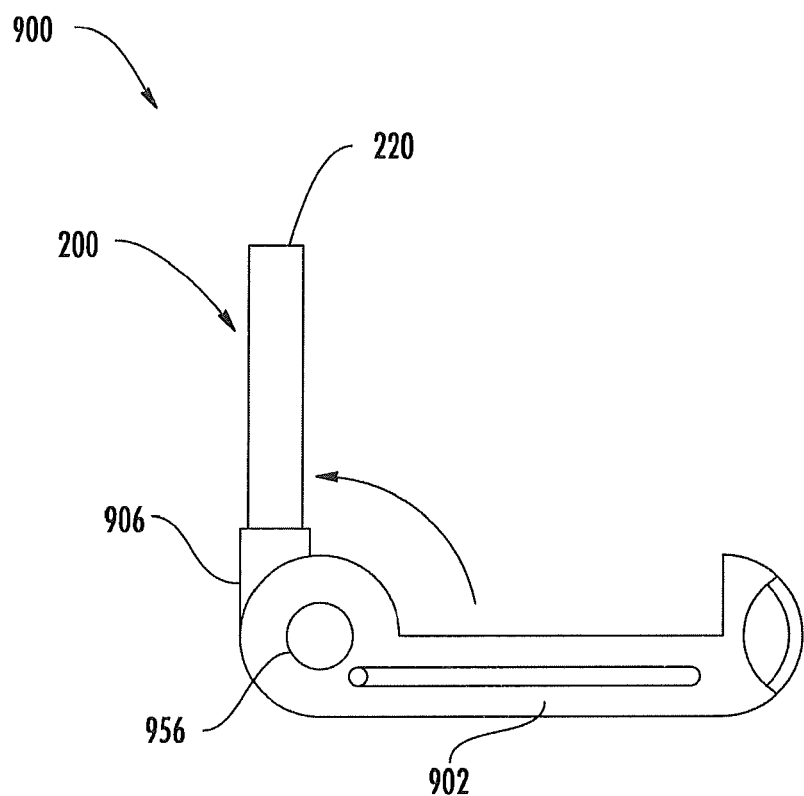
Figure 25:
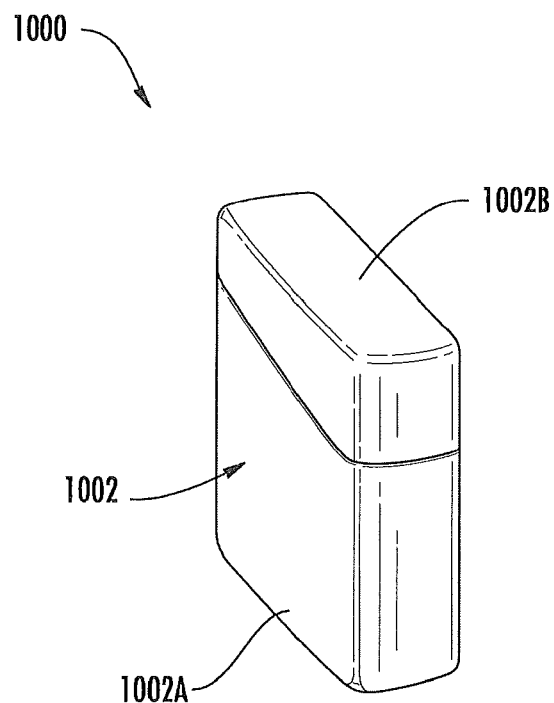
Figure 26:
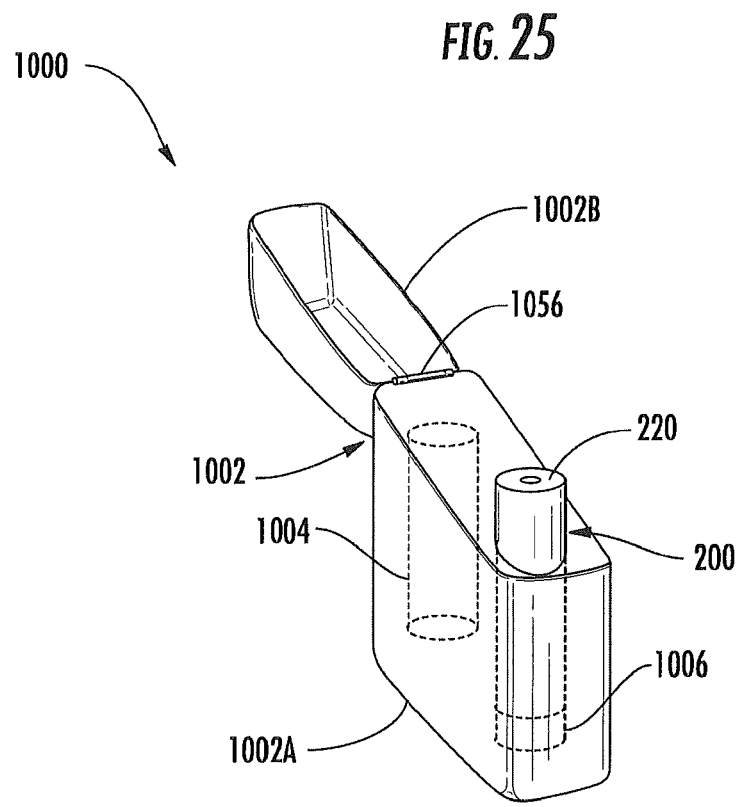
Figure 27:
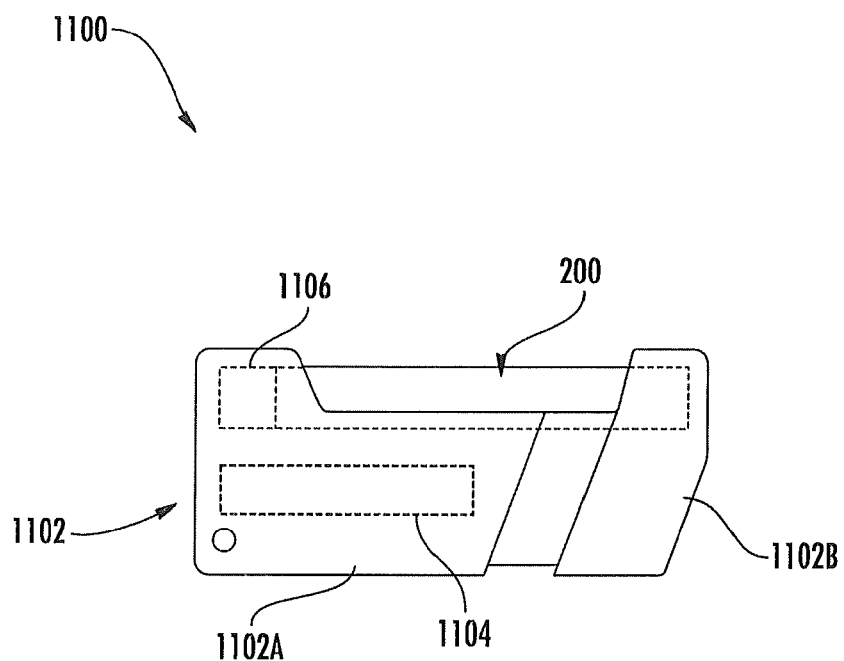
Figure 28:
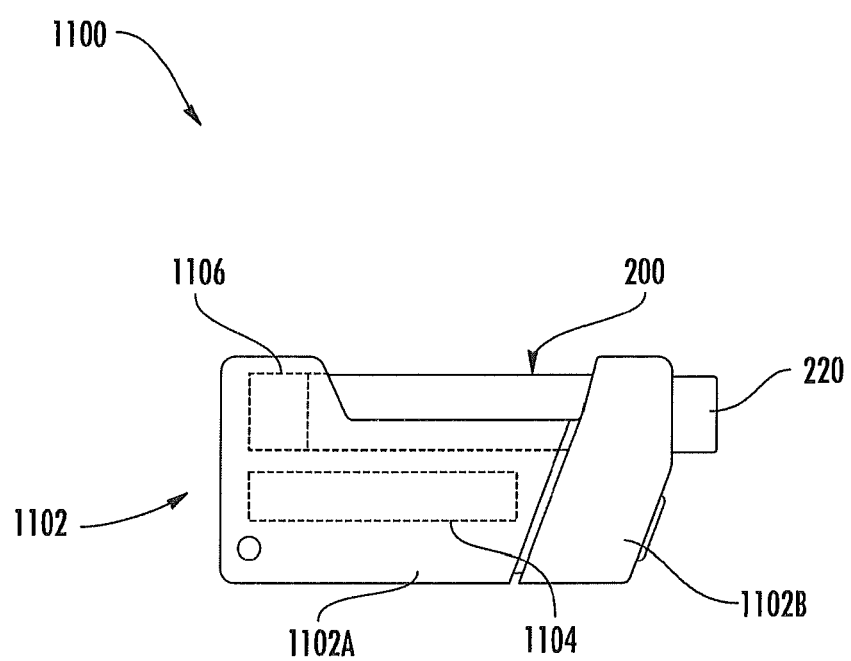
Figure 29:
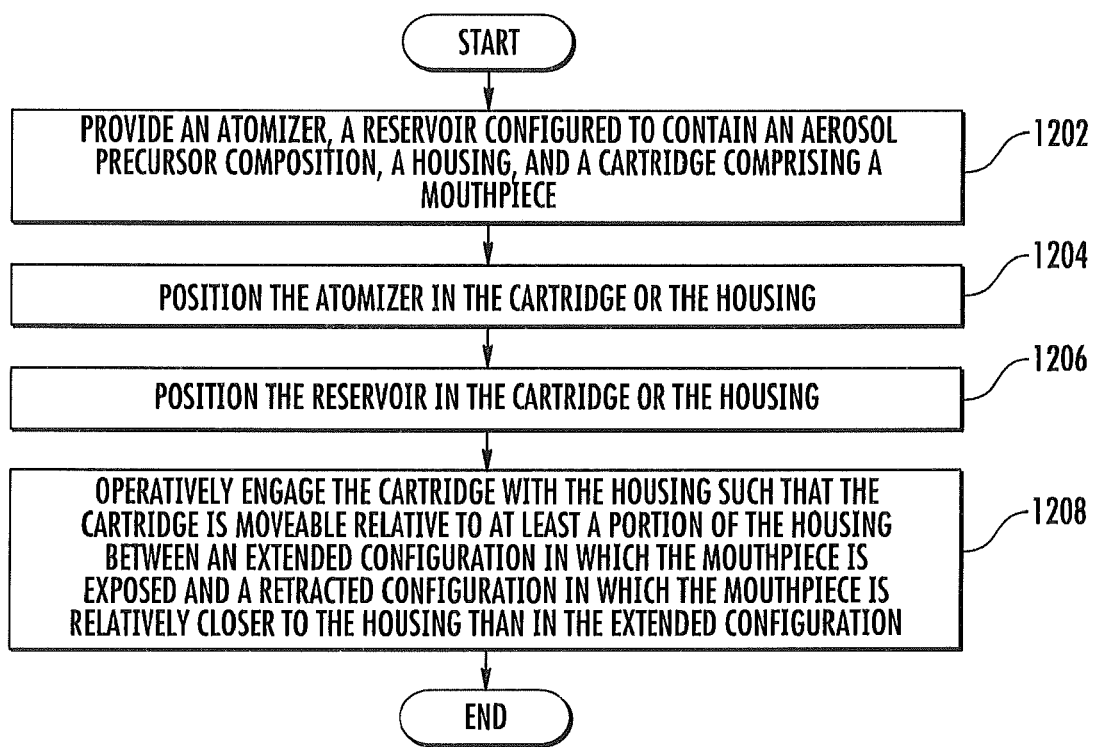
Figure 30:
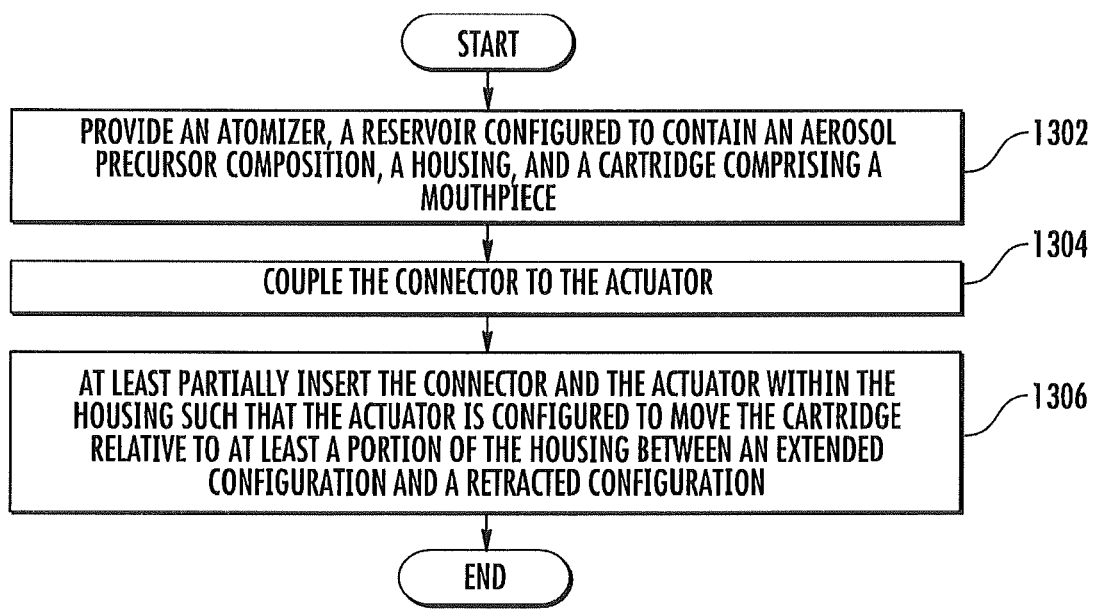
Figure 31:
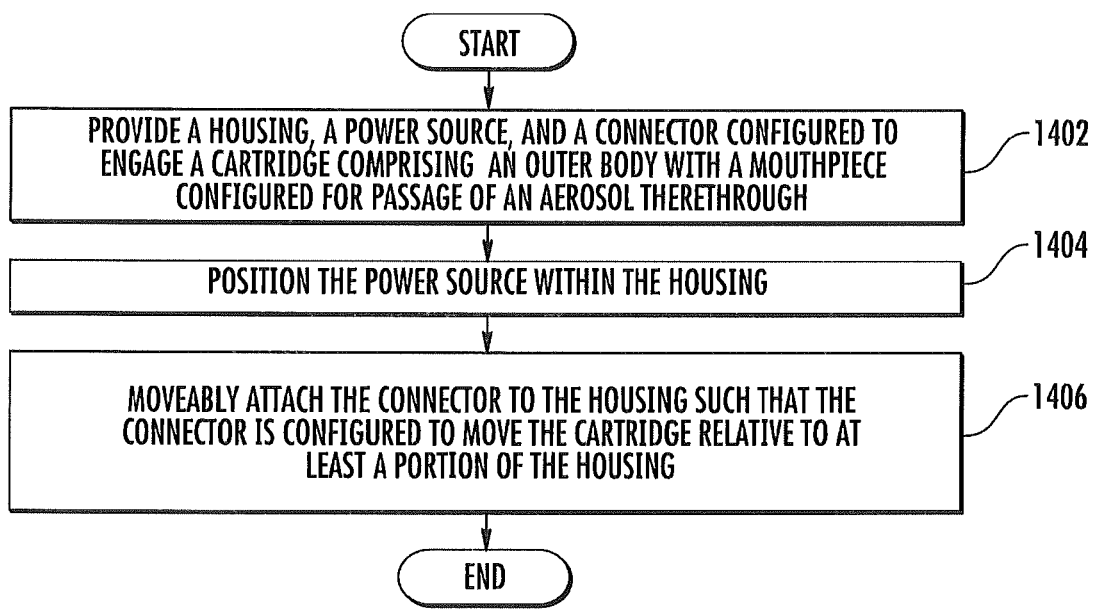
Figure 32:
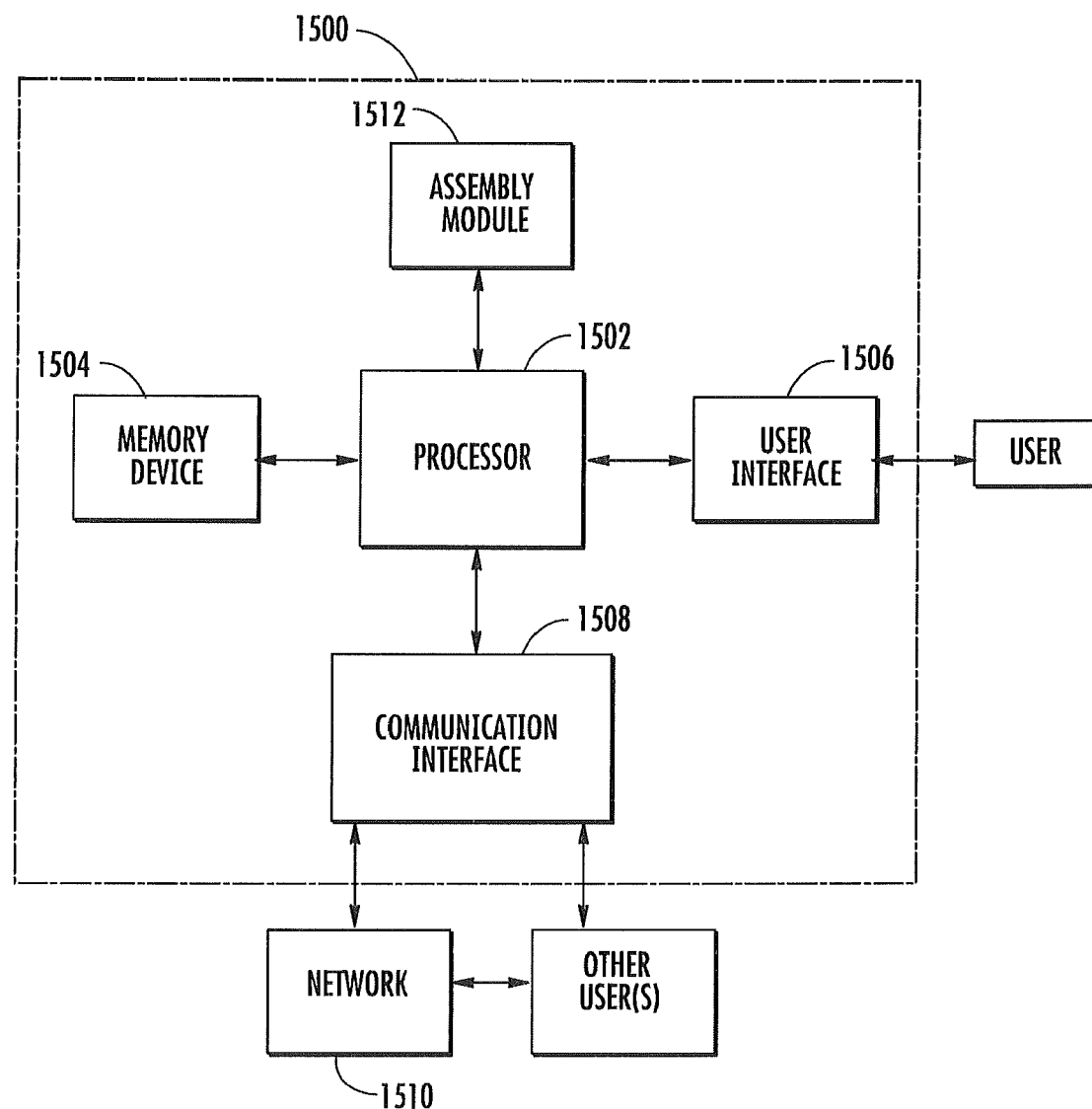

Having thus described the disclosure in the foregoing general terms, reference will now be made to the accompanying drawings, which are not necessarily drawn to scale, and wherein:

FIG. 1 schematically illustrates a sectional view through an aerosol delivery device comprising a housing and a cartridge wherein the cartridge is moveable relative to at least a portion of the housing and wherein the cartridge is in a retracted configuration according to an example embodiment of the present disclosure;

FIG. 2 schematically illustrates a front view of the aerosol delivery device of FIG. 1 wherein the cartridge is in an extended configuration;

FIG. 3 illustrates a cartridge suitable for use in the aerosol delivery device of FIG. 1 in an exploded configuration according to an example embodiment of the present disclosure;

FIG. 4 illustrates a perspective view of the aerosol delivery device of FIG. 1 wherein the cartridge is in the retracted configuration;

FIG. 5 illustrates an opposing perspective view of the aerosol delivery device of FIG. 1 wherein the cartridge is in the extended configuration;

FIG. 6 illustrates a rear perspective view of the aerosol delivery device of FIG. 1, wherein a rear cover of the housing is removed and the cartridge is in the retracted configuration;

FIG. 7 illustrates a front perspective view of the aerosol delivery device of FIG. 1, wherein a front cover of the housing is removed and the cartridge is in the extended configuration;

FIG. 8 illustrates a side perspective view of the aerosol delivery device of FIG. 1 wherein the front cover and the cartridge are removed;

FIG. 9 illustrates a perspective view of a slider of the aerosol delivery device of FIG. 1 in an exploded configuration;

FIG. 10 illustrates an opposing side perspective view of the aerosol delivery device of FIG. 1 wherein the front cover is removed and the cartridge is in the extended configuration;

FIG. 11 illustrates a side perspective view of the aerosol delivery device of FIG. 1 wherein the front cover is removed and the cartridge is in the retracted configuration;

FIG. 12 illustrates an enlarged perspective view of the slider and a controller of the aerosol delivery device of FIG. 1;

FIG. 13 illustrates an enlarged perspective view of a connector of the aerosol delivery device of FIG. 1;

FIG. 14 schematically illustrates a front view of an aerosol delivery device comprising a housing and a cartridge wherein the cartridge is moveable relative to at least a portion of the housing, wherein the cartridge is in an extended configuration, and wherein a bottom of the housing defines an attachment mechanism according to an example embodiment of the present disclosure;

FIG. 15 schematically illustrates a front view of an aerosol delivery device comprising a housing and a cartridge wherein the cartridge is moveable relative to at least a portion of the housing, wherein the cartridge is in an extended configuration, and wherein a corner of the housing defines an attachment mechanism according to an example embodiment of the present disclosure;

FIG. 16 schematically illustrates a perspective view of an aerosol delivery device comprising a housing and a cartridge wherein the cartridge is moveable relative to at least a portion of the housing, wherein the cartridge is in an extended configuration, and wherein a slider is configured to cover and uncover an opening according to an example embodiment of the present disclosure;

FIG. 17 schematically illustrates a sectional view through the aerosol delivery device of FIG. 16 wherein the cartridge is in a retracted configuration;

FIG. 18 schematically illustrates a sectional view through the aerosol delivery device of FIG. 16 wherein the cartridge is in the extended configuration;

FIG. 19 schematically illustrates a side view of an aerosol delivery device comprising a housing and a cartridge wherein the cartridge is moveable relative to at least a portion of the housing, wherein a moveable portion of the housing is hingedly moveable with respect to a main body portion of the housing, and wherein the cartridge is in a retracted configuration according to an example embodiment of the present disclosure;

FIG. 20 schematically illustrates a side view of the aerosol delivery device of FIG. 20 wherein the cartridge is in the extended configuration;

FIG. 21 schematically illustrates a partial perspective view of an aerosol delivery device comprising a housing and a cartridge wherein the cartridge is moveable relative to at least a portion of the housing, wherein a moveable portion of the housing is configured to pivot with respect to a main body portion of the housing, and wherein the cartridge is in an extended configuration according to an example embodiment of the present disclosure;

FIG. 22 schematically illustrates a side view of an aerosol delivery device comprising a housing and a cartridge wherein the cartridge is moveable relative to at least a portion of the housing, wherein the actuator comprises a spring and a button, and wherein the cartridge is in an extended configuration according to an example embodiment of the present disclosure;

FIG. 23 schematically illustrates a side view of an aerosol delivery device comprising a housing and a cartridge wherein the cartridge is hingedly moveable relative to at least a portion of the housing and wherein the cartridge is in a retracted configuration according to an example embodiment of the present disclosure;

FIG. 24 schematically illustrates a side view of the aerosol delivery device of FIG. 23 in an extended configuration;

FIG. 25 schematically illustrates a perspective view of an aerosol delivery device comprising a housing and a cartridge wherein the cartridge is moveable relative to a moveable portion of a housing and stationary respect to a main body portion, wherein the moveable portion is configured to hingedly move with respect to the main body portion, and wherein the cartridge is in a retracted configuration according to an example embodiment of the present disclosure;

FIG. 26 schematically illustrates a perspective view of the aerosol delivery device of FIG. 25 wherein the cartridge is in an extended configuration;

FIG. 27 schematically illustrates a side view of an aerosol delivery device comprising a housing and a cartridge wherein the cartridge is moveable with respect to a moveable portion of a housing and stationary with respect to a main body portion, wherein the moveable portion is configured to slide toward and away from the main body portion, and wherein the cartridge is in a retracted configuration according to an example embodiment of the present disclosure;

FIG. 28 schematically illustrates the aerosol delivery device of FIG. 28 in an extended configuration;

FIG. 29 schematically illustrates a method for assembling an aerosol delivery device according to a first example embodiment of the present disclosure;

FIG. 30 schematically illustrates a method for assembling an aerosol delivery device according to a second example embodiment of the present disclosure;

FIG. 31 schematically illustrates a method for assembling an aerosol delivery device according to a third example embodiment of the present disclosure; and FIG. 32 schematically illustrates a controller according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

Aerosol delivery devices according to the present disclosure may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, an aerosol delivery device of the present disclosure can be hand-held by a user, a user can draw on a portion of the article for inhalation of aerosol produced by that article, a user can take puffs at selected intervals of time, and the like.

Smoking articles of the present disclosure generally include a housing and a number of additional components coupled thereto and/or positioned within the housing, some of the components being movable relative to the housing. The overall design of the housing can vary, and the overall size and shape of the housing can vary. The smoking articles can include a cartridge, which can be defined by an outer body or shell—e.g., an elongated body resembling the shape of a portion of a cigarette or cigar. For example, an outer shell or body of the cartridge can be substantially tubular in shape and, as such, resemble the shape of a conventional cigarette or cigar. In some embodiments, the housing may contain one or more reusable components (e.g., a rechargeable battery and various electronics for controlling the operation of that article), and the cartridge can be removable, refillable, and/or disposable.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw). When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience. A battery for use in the present devices may be replaceable and/or rechargeable and thus may be combined with any type of recharging technology, including connection to a typical alternating current electrical outlet, connection to a car charger (i.e., a cigarette lighter receptacle), and connection to a computer, such as through a universal serial bus (USB) cable or connector. Examples of electrical power sources are described in U.S. Pat. App. Pub. No. 2010/0028766 to Peckerar et al., the disclosure of which is incorporated herein by reference in its entirety.

An aerosol delivery device according to the present disclosure preferably incorporates a sensor or detector for control of supply of electric power to a heat generation element when aerosol generation is desired (e.g., upon draw during use). As such, for example, there is provided a manner or method for turning off the power supply to the heat generation element when the aerosol generating piece is not be drawn upon during use, and for turning on the power supply to actuate or trigger the generation of heat by the heat generation element during draw. For example, with respect to a flow sensor, representative current regulating components and other current controlling components including various microcontrollers, sensors, and switches for aerosol delivery devices are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al. and 2014/0060554 to Collet et al.; and U.S. patent application Ser. No. 13/837,542, filed Mar. 15, 2013, to Ampolini et al. and Ser. No. 14/209,191, filed Mar. 13, 2014, to Henry et al.; which are incorporated herein by reference in their entireties. Additional representative types of sensing or detection mechanisms, structures, components, configurations, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some embodiments, the aerosol delivery device can include an indicator, which may comprise one or more light emitting diodes. The indicator can be in communication with the control component through a connector circuit and illuminate, for example, during a user draw on the mouthend as detected by the flow sensor.

Various elements that may be included in the housing are described in U.S. application Ser. No. 14/193,961 to Worm et al., filed Feb. 28, 2014, which is incorporated herein by reference in its entirety. Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to a pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 to Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; and U.S. patent application Ser. No. 13/841,233 to DePiano et al., filed Mar. 15, 2013, each of which is incorporated herein by reference in its entirety.

The aerosol precursor composition, also referred to as a vapor precursor composition, may comprise a variety of components including, by way of example, any of a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference in their entireties. Other aerosol precursors which may be employed in the aerosol delivery device of the present disclosure include the aerosol precursors included in the VUSE® product by R. J. Reynolds Vapor Company, the BLU™ product by Lorillard Technologies, the Mistic Menthol product by Mistic Ecigs, and the Vype product by CN Creative Ltd. Also desirable are the so-called "Smoke Juices" for electronic cigarettes that have been available from Johnson Creek Enterprises LLC. Additional exemplary formulations for aerosol precursor materials that may be used according to the present disclosure are described in U.S. Pat. Pub. No. 2013/0008457 to Zheng et al., and U.S. Pat. Pub. No. 2013/0213417 to Chong et al., the disclosures of which are incorporated herein by reference in their entireties.

The aerosol delivery device preferably includes a reservoir. In some embodiments, a reservoir may comprise a container for storing a liquid aerosol precursor, a fibrous substrate, or a combination of a fibrous substrate and a container. A fibrous substrate suitable for use as a reservoir may comprise a plurality of layers of nonwoven fibers and may be formed substantially into the shape of a tube. For example, the formed tube may be shaped and sized for placement within the outer body or shell of a cartridge for use in the aerosol delivery device. Liquid components, for example, can be sorptively retained by the fibrous substrate and/or be retained within a reservoir container. The reservoir preferably is in fluid connection with a liquid transport element. Thus, the liquid transport element may be configured to transport liquid from the reservoir to a heating element, such as via capillary action and/or via active transport—e.g., pumping or controlled movement with a valve. Representative types of substrates, reservoirs, or other components for supporting the aerosol precursor are described in U.S. Pat. No. 8,528,569 to Newton; and U.S. patent application Ser. No. 13/802,950 to Chapman et al., filed Mar. 15, 2013; Ser. No. 14/011,192 to Davis et al., filed Aug. 28, 2013; and Ser. No. 14/170,838 to Bless et al., filed Feb. 3, 2014; which are incorporated herein by reference in their entireties.

The liquid transport element may be in direct contact with the heating element. Various wicking materials, and the configuration and operation of those wicking materials within certain types of aerosol delivery devices, are set forth in U.S. patent application Ser. No. 13/754,324 to Sears et al., filed Jan. 30, 2013, which is incorporated herein by reference in its entirety. A variety of the materials disclosed by the foregoing documents may be incorporated into the present devices in various embodiments, and all of the foregoing disclosures are incorporated herein by reference in their entireties.

The heating element may comprise a wire defining a plurality of coils wound about the liquid transport element. In some embodiments the heating element may be formed by winding the wire about the liquid transport element as described in U.S. Pat. App. Pub. No. 2014/0157583 to Ward et al, which is incorporated herein by reference in its entirety. Further, in some embodiments the wire may define a variable coil spacing, as described in U.S. patent application Ser. No. 13/827,994 to DePiano et al., filed Mar. 14, 2013, which is incorporated herein by reference in its entirety. Various embodiments of materials configured to produce heat when electrical current is applied therethrough may be employed to form the heating element. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). In some embodiments, a stamped heating element may be employed in the atomizer, as described in U.S. patent application Ser. No. 13/842,125 to DePiano et al., filed Mar. 15, 2013, which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. App. Pub. No. 2014/0060554 to Collett et al., which is incorporated herein by reference, as noted above.

A variety of heater components may be used in the present aerosol delivery device. In various embodiments, one or more microheaters or like solid state heaters may be used. Embodiments of microheaters and atomizers incorporating microheaters suitable for use in the presently disclosed devices are described in U.S. Pat. App. Pub. No. 2014/0060554 to Collett et al., which is incorporated herein by reference in its entirety.

One or more heating terminals (e.g., positive and negative terminals) may connect to the heating element so as to form an electrical connection with the power source and/or a terminal may connect to one or more control elements of the aerosol delivery device. Further, various examples of electronic control components and functions performed thereby are described in U.S. Pat. App. Pub. No. 2014/0096781 to Sears et al., which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In further embodiments, one or more components of the aerosol delivery device may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the battery and controller. An example embodiment of a carbon-based cartridge is provided in U.S. Pat. App. Pub. No. 2013/0255702 to Griffith et al., which is incorporated herein by reference in its entirety.

Aerosol delivery devices are often configured in a manner that mimics aspects of certain traditional smoking devices such as cigarettes or cigars. In this regard, aerosol delivery devices typically define a substantially cylindrical configuration. For example, aerosol delivery devices often include a control body and a cartridge which attach in an end-to-end relationship to define the substantially cylindrical configuration. While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, the cylindrical configuration may result in the mouthpiece being exposed to the surrounding environment and therefore susceptible to contamination. Accordingly, it may be desirable to provide aerosol delivery devices in configurations that differ from shapes associated with traditional smoking articles.

In this regard, FIG. 1 schematically illustrates a modified sectional view through an aerosol delivery device 100 according to an example embodiment of the present disclosure. As described hereinafter, the aerosol delivery device 100 may include some or all of the components described above with respect to various embodiments of aerosol delivery devices.

As illustrated, in one embodiment the aerosol delivery device 100 may include a housing 102 and a cartridge 200. In some embodiments the cartridge 200 may be moveable with respect to at least a portion of, or an entirety of, the housing 102. In particular, the cartridge 200 may be moveable relative to at least a portion of the housing 102 between a retracted configuration illustrated in FIG. 1 and an extended configuration illustrated in FIG. 2. Details with respect to the mechanisms and manners associated with movement of the cartridge 200 relative to the housing 102 are described hereinafter.

In some embodiments, one or both of the housing 102 and the cartridge 200 may be referred to as being disposable or as being reusable. The aerosol delivery device 100 may include various other components disposed within the housing 102 or the cartridge 200 or otherwise coupled thereto. These components may be distributed between the housing 102 and the cartridge 200 in any of various manners. Accordingly, it should be understood that the described embodiments are provided for example purposes only.

One example embodiment of the cartridge 200 is illustrated in FIG. 3. As illustrated, the cartridge 200 may comprise a base shipping plug 202, a base 204, a control component terminal 206, an electronic control component 208, a flow tube 210, an atomizer 212, a reservoir substrate 214, an outer body 216, a label 218, a mouthpiece 220, and a mouthpiece shipping plug 222 according to an example embodiment of the present disclosure. The base 204 may be coupled to a first end of the outer body 216 and the mouthpiece 220 may be coupled to an opposing second end of the outer body to at least partially enclose the remaining components of the cartridge 200 therein, with the exception of the label 218, the mouthpiece shipping plug 222, and the base shipping plug 202. The base 204 may be configured to engage an associated device including a power source. In some embodiments the base 204 may comprise anti-rotation features that substantially prevent relative rotation between the cartridge and associated device including a power source as disclosed in U.S. patent application Ser. No. 13/840,264 to Novak et al., filed Mar. 15, 2013, which is incorporated herein by reference in its entirety.

The base shipping plug 202 may be configured to engage and protect the base 204 prior to use of the cartridge 200. Similarly, the mouthpiece shipping plug 222 may be configured to engage and protect the mouthpiece 220 prior to use of the cartridge 200. The control component terminal 206, the electronic control component 208, the flow tube 210, the atomizer 212, and the reservoir substrate 214 may be retained within the outer body 216. The label 218 may at least partially surround the outer body 216 and include information such as a product identifier thereon.

The atomizer 212 may comprise a first heating terminal 234a and a second heating terminal 234b, a liquid transport element 238 and a heating element 240. In this regard, the reservoir substrate 214 may be configured to hold an aerosol precursor composition. The reservoir substrate 214 is in fluid connection with the liquid transport element 238 so as to transport liquid from the reservoir substrate 214 to the heating element 240 (e.g., via capillary action.

Various other details with respect to the components that may be included in the cartridge 200, are provided, for example, in U.S. patent application Ser. No. 13/840,264 to Novak et al., filed Mar. 15, 2013, which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heating terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow tube, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 20 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 21 thereof illustrates a perspective view of a base with an anti-rotation mechanism; FIG. 22 thereof illustrates a perspective view of a coupler with an anti-rotation mechanism; and FIG. 23 thereof illustrates a sectional view through the base of FIG. 21 thereof and the coupler of FIG. 22 thereof in an engaged configuration.

In another embodiment the cartridge 200 may be substantially similar, or identical, to the cartridge disclosed in U.S. patent application Ser. No. 14/286,552 to Brinkley et al., filed May 23, 2014, which is incorporated herein by reference in its entirety. Thus, for example, the cartridge may include a flow director defining a non-tubular configuration, an electronics compartment sealed with respect to a reservoir compartment, and/or any of the various other features and components disclosed therein. Accordingly, it should be understood that the particular embodiment of the cartridge 200 described herein is provided for example purposes only. In this regard, the cartridge 200 is schematically illustrated in FIG. 1 as including only the outer body 216, the mouthpiece 220, the atomizer 212, the reservoir 214, and the base 204, in light of the various alternate and additional components that may be included therein.

Similarly, in one embodiment the housing 102 may include some or all of the components of existing embodiments of control bodies configured to engage the above-described cartridge 200 positioned therein or otherwise coupled thereto. For example, the housing 402 may include some or all of the components of the control bodies disclosed in U.S. patent application Ser. No. 13/840,264 to Novak, et al., filed Mar. 15, 2013, Ser. No. 14/286,552 to Brinkley et al., filed May 23, 2014, and Ser. No. 14/193,961 to Worm et al., filed Feb. 28, 2014, each of which is incorporated herein by reference in its entirety. However, as may be understood, the cartridge 200 may include some or all of these components in other embodiments.

By way of example, in the illustrated embodiment (see, e.g., FIG. 1) the aerosol delivery device 100 includes a power source 104 (e.g., a battery) positioned within the housing 102. Further, a connector 106 may be moveably attached to the housing 102. The cartridge 200 may be engaged with the connector 106 so as to be moveable relative to at least a portion of the housing 102. In some embodiments the cartridge 200 may be removably engaged with the connector 106 and replaceable. The aerosol delivery device 100 may additionally include a controller 108 received therein. The controller 108 may be configured to direct electrical power from the power source 104 to the cartridge 200 to heat the aerosol precursor composition retained in the reservoir 214 with the atomizer 212 to produce a vapor, which may occur during a user draw on the mouthpiece 220 of the cartridge.

One or more components of the cartridge 200 may be configured to form an electrical connection with the connector 106. For example, referring to the cartridge embodiment of FIG. 3, the first heating terminal 234a and the second heating terminal 234b (e.g., positive and negative terminals) at the opposing ends of the heating element 240 are configured to form an electrical connection with the connector 106. Further, the electronic control component 208 (see, FIG. 3) may form an electrical connection with the connector 106 through the control component terminal 206 (see, FIG. 3). Components within the housing 102 (e.g., the controller 108) may thus employ the electronic control component 208 to determine whether the cartridge 200 is genuine and/or perform other functions. However, in other embodiments the connection between the connector 106 and the cartridge 200 may not be electrical. In other words, the connection between the connector 106 and the cartridge 300 may be purely mechanical. In these embodiments atomization may occur outside of the cartridge or atomization may occur via other methods not requiring electrical connections between the cartridge and the housing such as via piezoelectric or radio frequency atomization. Alternatively, the power source may be positioned in the cartridge such that electrical connection with connector is not required.

During use, a user may draw on the mouthpiece 220 of the cartridge 200 of the aerosol delivery device 100. This may pull air through an opening in the connector 106 or in the cartridge 200. However, the flow of air may be received through other parts of the aerosol delivery device 100 in other embodiments. As noted above, in some embodiments the cartridge 200 may include the flow tube 210 (see, FIG. 3). The flow tube 210 may be configured to direct the flow of air to the heating element 240 (see, FIG. 3) of the atomizer 212.

As described below, a sensor in the aerosol delivery device 100 may sense the puff. When the puff is sensed, the controller 108 may direct current to the heating element 240 through a circuit including the first heating terminal 234a and the second heating terminal 234b (see, FIG. 3). Accordingly, the heating element 240 may vaporize the aerosol precursor composition directed to an aerosolization zone from the reservoir substrate 214 by the liquid transport element 238 (see, FIG. 3). Thus, the mouthpiece 220 may allow passage of aerosol (i.e., the components of the aerosol precursor composition in an inhalable form) therethrough to a consumer drawing thereon.

As noted above, the cartridge 200 may be moveable relative to the housing 102. In this regard, the aerosol delivery device 100 may further comprise an actuator 110. In particular, the actuator 110 may be coupled to the connector 106. Thereby, the actuator 110 may be operatively engaged with the cartridge 200 and configured to move the cartridge between the extended configuration and the retracted configuration.

As illustrated in FIG. 2, the mouthpiece 220 may be exposed when the cartridge 200 is in the extended configuration. In other words the mouthpiece 220 may be positioned outside of the housing 102 when the cartridge 200 is in the extended configuration such that a user may engage the mouthpiece with his or her lips. Thus, the extended configuration of the cartridge 200 is a configuration in which the aerosol delivery device 100 is configured to receive a draw on the mouthpiece 220 such that the aerosol delivery device may produce and deliver an aerosol to a user in the manner described above.

Conversely, as illustrated in FIG. 1, in the retracted configuration the mouthpiece 220 is relatively closer to the housing 102 than in the extended configuration (see, FIG. 2). In the retracted configuration the mouthpiece 220 may be flush with respect to the housing 102. In other words, an outer surface of the mouthpiece 220 may substantially align with an outer surface of the housing 102. In another embodiment the mouthpiece 220 may be recessed with respect to the housing 102. In other words, a gap may be provided between the outer surface of the mouthpiece 220 and the outer surface of the housing 102.

Thus, in one embodiment the mouthpiece 220 of the cartridge 200 may be at least partially received within the housing 102 in the retracted configuration. In another embodiment an entirety of the cartridge 200 including the mouthpiece 220 may be received within the housing 102 in the retracted configuration. Accordingly, by positioning the mouthpiece 220 relatively closer to the housing 102 (e.g., partially or entirely received therein), the mouthpiece may be protected from damage. Further, the mouthpiece 220 may be less prone to contamination (e.g., from lint, dust, or dirt) in the retracted configuration, which might otherwise transfer to a user's lips or contact the heating element, which could adversely affect performance thereof. Additionally, in the retracted configuration fluid leakage out of the mouthpiece 220 of the cartridge 200 (e.g., condensation) may be captured by the housing 102. For example, fluid leaking from the mouthpiece 220 may drain into a surrounding portion of the housing 102, at which the fluid may be retained and evaporate. In contrast, aerosol delivery devices defining configurations resembling traditional smoking articles typically include a fixedly-positioned mouthpiece, which may be exposed to its surroundings and thereby susceptible to damage or contamination if not properly stored by a user, and which may leak fluid (e.g., condensation) to its surroundings in certain instances.

As noted above, embodiments of the present disclosure relate to aerosol delivery devices that include a cartridge that is moveable with respect to at least a portion of a housing between a retracted configuration and an extended configuration. As further noted above, such aerosol delivery devices may include any of a wide variety of components as described elsewhere herein. However, embodiments of aerosol delivery devices including example configurations of components are described hereinafter. Again, however, it should be understood that the illustrated configurations are provided for example purposes only. Thus, a greater or lesser number of components and/or the same or differing components, which may be distributed between the cartridge and the housing in the same or differing manners, may be included in embodiments of aerosol delivery devices of the present disclosure. By way of further example, in one embodiment the reservoir and/or the heater may be positioned in the housing, rather than in the cartridge. In this embodiment the cartridge may deliver aerosol formed in the housing to the user, rather than produce the formed aerosol. Thus, the cartridge may substantially define a straw, tube, or the like on which the user draws in some embodiments.

However, by way of example, FIGS. 4-13 illustrate views of the aerosol delivery device 100 of FIGS. 4 and 5 including additional components according to an example embodiment of the present disclosure. In particular, FIG. 4 illustrates a perspective view of the aerosol delivery device 100 in the closed configuration and FIG. 5 illustrates a perspective view of the aerosol delivery device in the extended configuration. As illustrated, the housing 102 may define an ergonomic shape configured to comfortably fit within a user's hand. In this regard, the housing 102 may define a bottom 102A and a top 102B that are oppositely disposed from one another, first and second sides 102C, 102D that are oppositely disposed from one another, and a front 102E and a rear 102F that are oppositely disposed from one another. The bottom 102A may be curved and the sides 102C, 102D may taper toward the top 102B to facilitate gripping the aerosol delivery device 100 in the palm of a user's hand. The shape of the housing 102, however, is not limited and may be any shape that accommodates the various elements as described herein.

Additionally, in some embodiments the housing 102 may comprise a front cover 102G and a rear cover 102H. The front cover 102G may define the front 102E of the housing 102. Conversely, the rear cover 102H may define the rear 102F of the housing 102.

Further, the housing 102 may define a width extending between the sides 102C, 102D from about 20 mm to about 60 mm, a thickness extending between the front 102E and the back 102F from about 10 mm to about 50 mm, and a length extending between the bottom 102A and the top 102B from about 40 mm to about 120 mm. In some embodiments, the housing may be expressly non-cylindrical. In contrast, typical aerosol delivery devices configured to resemble traditional smoking articles (e.g., cigarettes) are substantially cylindrical in shape and may define a diameter from about 8 mm to about 15 mm and a longitudinal length from about 80 mm to about 120 mm. Accordingly, the width of the aerosol delivery devices of the present disclosure may be substantially greater than the diameter of traditional aerosol delivery devices in order to improve the level of comfort and secureness of grip associated with grasping the aerosol delivery devices of the present disclosure. Conversely, the length of the aerosol delivery devices of the present disclosure (in the retracted configuration) may be less than the length of traditional aerosol delivery devices in order to improve the portability of the aerosol delivery devices of the present disclosure.

As further illustrated in FIG. 5, the aerosol delivery device 100 may additionally include an attachment mechanism 112. The attachment mechanism 112 may comprise a loop, a clip, a ring, or other mechanism configured to attach to another device such as a keychain, a carabineer, or a lanyard. Accordingly, the aerosol delivery device 100 may be retained in a desired position. Thus, for example, a user may be able to more easily secure the aerosol delivery device 100 in a desired position at which the aerosol delivery device may be less prone to damage or misplacement. The attachment mechanism 112 may be positioned substantially opposite from an end of the housing 102 at which the cartridge 200 extends therefrom (e.g., at the top 102B) so as to avoid interference with a user drawing on the cartridge during use.

The aerosol delivery device 100 may additionally include an input mechanism 114. The input mechanism 114 may comprise a button or switch configured to receive an input from a user. When the input mechanism 114 is actuated, the aerosol delivery device 100 may produce an output corresponding to a status of the aerosol delivery device. For example, the aerosol delivery device may output sound, vibration, or light. As illustrated in FIG. 4, the aerosol delivery device 100 may further comprise an indicator 116. The indicator 116 may comprise a light transmitter 116A (e.g., plastic or glass, which may be tinted a desired color). Further, the indicator 116 may include a light emitter 116B (see, e.g., FIG. 6), which may comprise an incandescent bulb or light emitting diode (LED). Thereby, the light emitter 116B may illuminate the light transmitter 116A, which may direct the light outwardly therethrough to output a status of the aerosol delivery device 100.

In this regard, the indicator 116 may flash or otherwise illuminate to indicate a remaining or used portion of the capacity of the power source 104 or the reservoir 214 (see, e.g., FIG. 1). For example, a relatively large number of flashes of the indicator 116 upon actuation of the input mechanism 114 may correspond to a relatively large remaining capacity of the power source 104 or the reservoir 214 (see, e.g., FIG. 1). Conversely, a relatively small number of flashes of the indicator 116 upon actuation of the input mechanism 114 may correspond to a relatively small remaining capacity of the power source 104 or the reservoir 214 (see, e.g., FIG. 1). However, the indicator 116 and/or other output mechanisms may be employed to output various other information and/or output information in various other manners. Examples of other information that may be outputted include error messages, operational modes, historical usage information, etc.

Further in some embodiments the aerosol delivery device 100 may include a display 118, as illustrated in FIG. 5. The display 118 may be provided in addition to, or as an alternate for, the indicator 116. In this regard, the display 118 may be configured to output various information including information regarding a status of the aerosol delivery device 100, information unrelated to the status of the aerosol delivery device (e.g., the present time), and/or non-informative graphics (e.g., graphics provided for user entertainment purposes). Thereby, the display 118 may be configured to output any or all of the information described above (e.g., a remaining or used portion of the capacity of the power source 104 or the reservoir 214) in any form such as graphical form and/or a numerical form. Further, in some embodiments operation or the display may be controlled by the input mechanism 114 or a separate input mechanism. The display 118, for example, may be a touchscreen and thus may be configured for user input. In some embodiments, the display 118 may provide icons, menus, or the like configured to allow a user to make control selections related to the functioning of the aerosol delivery device 100, check a specific status of the device, or the like. Although the display 118 is illustrated as encompassing only a relatively small portion of the front cover 102G, it is understood that the display may cover a significantly greater portion of the front cover and/or the rear cover 102H.

FIG. 6 illustrates a rear perspective view of the aerosol delivery device 100 with the rear cover 10211 (see, FIGS. 6 and 7) removed for illustration purposes, wherein the cartridge 200 is in the retracted configuration. FIG. 7 illustrates a front perspective view of the aerosol delivery device 100 with the front cover 102G (see, FIGS. 6 and 7) removed for illustration purposes, wherein the cartridge 200 is in the extended configuration. Accordingly, various internal components of the aerosol delivery device 100 are illustrated in FIGS. 8 and 9.

As previously noted, the actuator 110 may be operatively engaged with the cartridge 200 and configured to move the cartridge between the extended configuration and the retracted configuration. Various embodiments of the actuator 110 may be employed. However, in one embodiment, as illustrated in FIGS. 8 and 9, the actuator 110 comprises a slider 120. The slider 120 may be configured to translate or otherwise move between a first position at which the cartridge 200 is in the extended configuration (see, e.g., FIG. 7) and a second position at which the cartridge is in the retracted configuration (see, e.g., FIG. 6).

The slider 120 may be configured to slide upon a track 122 between the first and second positions. In this regard, a user may slide the slider 120 between the first and second positions via direct or indirect engagement therewith. For example, in the illustrated embodiment the actuator 110 includes an external engagement member 124 (see, e.g., FIG. 7) coupled to the slider 120 and configured for engagement by a user (e.g., configured for engagement by a user's thumb) in order to allow the user to move the slider 120. In this regard, the external engagement member 124 may be positioned or extend outside of the housing 102. In the illustrated embodiment the external engagement member 124 extends out of the front 102E of the housing 102 (see, e.g., FIG. 7). However, the external engagement member 124 may extend out of any other portion of the housing 102 in other embodiments. For example, the actuator 110 may be configured to extend out of one of the sides 102C, 102D of the housing 102. Further, a concealment member 126 (see, e.g., FIG. 7) may limit exposure of internal components of the aerosol delivery device 100 to an external environment, as described in detail below.

The track 122 may guide movement of the slider 120 thereon. The track 122 may restrain motion of the slider 120 such that the slider may move only in first and second directions along the longitudinal length of the track. Various embodiments of the track 122 and the slider 120 may be employed to allow for movement in this manner. However, details with respect to one example embodiment of the track 122 and the slider 120 are illustrated in FIG. 8, in which various components including the cartridge 200, the front cover 102G (see, FIGS. 6 and 7), the external engagement member 124 (see, e.g., FIG. 7), and the concealment member 126 (see, e.g., FIG. 7) are not shown for illustration purposes.

As illustrated, the track 122 may define a longitudinal extension 128 and the slider 120 may define a slot 130 configured to receive the longitudinal extension therein. Accordingly, lateral motion of the slider 120, perpendicular to the longitudinal length of the longitudinal extension 128 may be substantially avoided while allowing the slider to move along the longitudinal length thereof. Further, the longitudinal movement of the slider 120 may be limited.

As illustrated in FIGS. 6 and 7, in one embodiment the longitudinal travel of the slider 120 is limited by contact between the external engagement member 124 and first and second longitudinal ends of an opening 132 defined through the front cover 102G. However in other embodiments travel of the slider 120 may be limited in other manners. For example, the track 122 may define a stop at one or both ends thereof, the housing 102 may define a stop at one or both ends of the track, or any of various other components may define a stop configured to engage the slider 120 and/or the external engagement member 124 to limit travel of the actuator along the track.

In order to guide movement of the cartridge 200, in some embodiments the aerosol delivery device 100 may further comprise a guide member 134, as illustrated in FIG. 6. The guide member 134 may provide the cartridge 200 with additional stability within the housing 102 and ensure axial movement of the cartridge 200 along a longitudinal axis thereof during extension and retraction. Further, in some embodiments the guide member 134 may define a stop limiting extension of the cartridge, for example due to contact between a connector 106, which is described below, and the guide member. In one embodiment the guide member 134 may be defined by the housing 102. However, in other embodiments the guide member may comprise a separate component coupled to the housing.

In some embodiments the actuator 110 may define features configured to retain the slider 120 at a selected position along a longitudinal length of the track 122. For example, as illustrated in FIG. 8, in one embodiment the track 122 may define a detent or an indentation 136 in a side of the longitudinal extension 128. Further, as illustrated in FIG. 9, in one embodiment the slider 120 may include a protrusion 138. In the illustrated embodiment the protrusion comprises a ball bearing which is held in place inside an aperture 140 defined through the slider 120 and against a side of the longitudinal extension 128 of the track 122 (see, e.g., FIG. 8) by a set screw 142. By providing the protrusion 138 with a rounded configuration, the protrusion may releasably engage the indentation 136 without causing damage thereto.

A position of the indentation 136 (see, FIG. 8) may be selected such that when the protrusion 138 (see, FIG. 9) engages the indentation, the cartridge 200 is at a selected position with respect to the housing 102. For example, in the illustrated embodiment when the protrusion 138 engages the indentation 136, the cartridge 200 is in the extended configuration (see, e.g., FIG. 7). Conversely, the track 122 may additionally or alternatively include an indentation configured to releasably retain the cartridge in the retracted configuration (see, e.g., FIG. 6). By releasably retaining the cartridge 200 in the extended configuration and/or the retracted configuration, accidental extension or retraction of the cartridge 200 may be avoided. Further, embodiments employing the set screw 142 may allow for adjustment of the amount of force required to move the slider 120 along the track 122. In this regard, the set screw 142 may be tightened to increase the force required to move the slider 120, or loosened to reduce the amount of force required to move the slider. Note that in other embodiments the configuration of the indentation and the protrusion may be reversed such that the track defines a protrusion and the slider includes an indentation. Further, various other mechanisms may be configured to releasably retain the slider at one or more positions along the length of the track. For example, magnets may be employed to retain the slider at one or more positions along the track.

In other embodiments the indentation 136 and the protrusion 138 may not be included and retention of the slider 120 in a selected position may be caused by frictional engagement between the slider 120 and the track 122. For example, the slot 130 defined by the slider 120 may be dimensioned so as to tightly fit over the longitudinal extension 128 of the track 122 (see, e.g., FIG. 8). In this regard, when a user moves the slider 120 on the track 122 to cause the cartridge 200 to move to the extended configuration or the retracted configuration, frictional engagement between the slider and the track may cause the slider to remain at the selected position along the track until the user moves the slider to another position. Accordingly, accidental extension or retraction of the cartridge 200 may be avoided in other manners. However, usage of the indentation 136 and the protrusion 138 may provide a variable degree of resistance associated with moving the slider 120, in addition to more secure retention of the slider in a selected position, which users may find to be more satisfying during use.

As noted above, the actuator 112 may include the concealment member 126 (see, e.g., FIG. 5) in some embodiments. The concealment member 126 may be configured to limit exposure of internal components of the aerosol delivery device 100 to contaminants. Further, the concealment member 126 may be configured to limit the visibility of, and access to, the internal components of the aerosol delivery device 100.

In this regard, as illustrated in FIG. 5, the concealment member 126 may be configured to block (e.g., overlap with) at least a portion of the opening 132 defined through the front cover 102G. The concealment member 126 may define an opening 144 which allows for movement of the slider 120 via the external engagement member 124 so as to move the cartridge 200 between the retracted configuration (see, e.g., FIG. 4) and the extended configuration (see, e.g., FIG. 5), as described above. However, the opening 144 through the concealment member 126 may be relatively smaller than the opening 132 through the front cover 102G.

In this regard, as illustrated in FIG. 7, the actuator 110 may further comprise one or more fasteners 146 (e.g., screws or rivets) which extend through the external engagement member 124 and the opening 144 through the concealment member 126 into the slider 120 so as to couple the external engagement member to the slider. Thereby, the opening 144 through the concealment member 126 may define a width, transverse to a longitudinal length thereof, which is slightly greater than the width of the fasteners 146 to allow for sliding movement of the fasteners 146 within the opening through the concealment member. Accordingly, the opening 144 through the concealment member 126 may be relatively narrower than the opening 132 through the front cover 102G (see, e.g., FIG. 5), which may be slightly wider than a width of the external engagement member 124. However, as may be understood in other embodiments one or both of the slider 120 and the external engagement member 124 may define a relatively narrow portion configured to extend through the opening 132 through the concealment member 126. Additionally, in some embodiments the slider 120 and the external engagement member 124 may define a unitary component, as opposed to separate pieces coupled to one another by fasteners.

As illustrated in FIG. 5, in the extended configuration the open area defined by the opening 144 through the concealment member 126 may be relatively small, and in particular smaller than the area defined by the opening 132 through the housing 102. Further, as illustrated in FIG. 4, in the retracted configuration the opening 144 (see, e.g., FIG. 5) through the concealment member 126 may be substantially entirely covered by the external engagement member 124. In this regard, the aerosol delivery device 100 may be stored in the retracted configuration, and hence more likely to be exposed to dust, debris, and other contaminants while in the retracted configuration. Thus, by substantially or entirely closing the opening 144 through the concealment member 126 in the retracted configuration, entry of contaminants through the opening 144 through the concealment member 126 may be substantially avoided.

In this regard, as illustrated in FIGS. 10 and 11, the slider 120 may include a primary portion 120A, an extension 120B, and a connector portion 120C. The connector portion 120C of the slider 120 may connect the extension 120B to the primary portion 120A. In particular, the connector portion 120C of the slider 120 may be positioned at a distal end of the extension 120B such that the extension may extend therefrom and overhang the primary portion 120A in one direction so as to produce an open gap 148 between the primary portion and the extension.

The open gap 148 may allow for increased travel of the slider 120 along the track 122 during movement of the cartridge 200 to the extended configuration without requiring a corresponding increase in the longitudinal length of the opening 144 in the concealment member 126 (see, e.g., FIG. 7). In this regard, as illustrated in FIG. 10, the extension 120B may overlap with a portion of the concealment member 126 in the extended configuration. Use of the open gap 148 (see, e.g., FIG. 8) defined between the extension 120B and the primary portion 120A of the slider 120 in conjunction with the relatively smaller opening 144 in the concealment member 126 may better conceal internal components of the aerosol delivery device 100 and reduce the possibility of entry of contaminants therethrough as compared to usage of a relatively larger opening.

Additionally, in some embodiments the concealment member 126 may be configured to slide in first and second opposing longitudinal directions. In this regard, as the slider 120 slides in a first direction to cause the cartridge 200 to move to the extended configuration, the concealment member 126 may also slide in the first direction (e.g., generally to the left in terms of the orientation illustrated in FIG. 10) when a first side the connector portion 120C of the slider contacts the concealment member at an end of the opening 132 therethrough. Conversely, when the slider 120 is moved in an opposing second direction, opposite to the first direction, in order to move the cartridge 200 to the retracted configuration illustrated in FIG. 11, an opposing second side of the connector portion 120C of the slider may engage the concealment member 126 at an opposing end of the opening 132 therethrough. Accordingly, the concealment member 126 may be moved in an opposing second direction (e.g., generally to the right in terms of the orientation illustrated in FIG. 11). By allowing the concealment member 126 to slide in this manner, the longitudinal length of the opening 132 therethrough necessary to allow full extension and retraction of the cartridge 200 may be reduced. Note that in order to allow for movement of the concealment member 126 while still substantially blocking the opening 132 defined through the front cover 102G (see, e.g., FIG. 5), the concealment member 126 may define a longitudinal length that is greater than a longitudinal length of the opening through the front cover. In particular, the longitudinal length of the concealment member 126 may be at least equal to the longitudinal length of the opening 132 defined through the front cover 102G plus a length of the stroke of the concealment member during movement of the cartridge 200 between the retracted configuration and the extended configuration.

As noted above, in the retracted configuration (see, e.g., FIG. 4) the opening 144 (see, e.g., FIG. 5) through the concealment member 126 may be substantially entirely covered by the external engagement member 124. In this regard, as illustrated in FIG. 4, in some embodiments the external engagement member 124 may define a tab 124A. The tab 124A may be configured to cover any remaining portion of the opening 144 (see, e.g., FIG. 5) through the concealment member 126 that is not covered by a body portion 124B of the external engagement member 124. The tab 124A may be configured to slide under the front cover 102G inside the housing 102 during movement of the cartridge 200 into the extended configuration (see, e.g., FIG. 5). In one embodiment, the tab 124A may function as a child lock. In this regard, in order to fully extend the cartridge 200, a user may be required to depress the external engagement member 124 inwardly while sliding the external engagement member such that the tab 124A is able to slide under the front 102E of the housing 102, rather than into abutting contact therewith, which may be required for operation of the aerosol delivery device 100 in some embodiments. However, as may be understood, the actuator 110 may be configured with various other safety mechanisms configured to prevent usage of the aerosol delivery device by a child and/or accidental extension of the cartridge or actuation of the aerosol delivery device, which may require depression of the actuator during usage or other complex or force-intensive manipulations of the actuator and/or a separate member (e.g., a lockout switch).

As noted above, the aerosol delivery device 100 may employ the connector 106 to cause movement of the cartridge 200 when the actuator 110 is displaced. As illustrated in FIG. 7, the connector 106 may be coupled to a portion of the actuator 110 that is displaced when a user moves the external engagement member 124. For example, as illustrated in FIG. 6, the connector 106 may be coupled to the slider 120. Thereby, when the external engagement member 124 displaces the slider 120, the slider may displace the connector 106, which in turn displaces the cartridge 200.

In this regard, the connector 106 may be configured to mechanically engage the cartridge 200 such that the cartridge is firmly coupled therewith. Various mechanisms may connect the cartridge 200 to the connector 106 to result in a threaded engagement, a press-fit engagement, an interference fit, a magnetic engagement, or the like. Further, the connector 106 may be configured to form an electrical connection between the cartridge 200 and the controller 108. Thereby, for example, current may be delivered to the atomizer 212 and the electronic control component 208 (see, e.g., FIG. 3) in embodiments in which an electronic control component is included in the cartridge 200 (e.g., for cartridge authenticity verification purposes). Note that although the controller 108 is illustrated as being coupled to the slider 120 and the connector 106, and hence configured to move therewith, in other embodiments the controller may fixedly positioned with respect to the housing 102 and an interconnecting member may electrically couple the cartridge 200 to the controller 108 through the connector 106. By way of example, the interconnecting member may comprise a flexible circuit board, a ribbon cable, one or more wires, a wire loop or bundle with or without sheathing, or a moving or sliding contact, brush, spring (e.g., leaf spring), spring pins (e.g., as employed in computer power connectors) and/or trace, which may be employed to form electrical connections between the cartridge and the controller. Thus, for example, in some embodiments the cartridge 200 may be partially or fully electrically disconnected from the controller 108 in the retracted configuration and electrically connected to the controller in the extended configuration. This configuration may ensure that unintended activation of the cartridge in the retracted configuration is not possible. Such a configuration may be advantageously employed in conjunction with the releasable retention mechanisms described above. However, in other embodiments the interconnecting member may maintain an electrical connection between the cartridge and the controller in both the retracted configuration and the extended configuration.

The connector 106 may include a coupler 150 (see, FIG. 8) configured to facilitate engagement with the cartridge 200 in the above-described manner. In some embodiments the coupler 150 may be configured to permanently engage the cartridge 200. For example, a permanent coupling between the coupler 150 and the cartridge 200 may be employed in embodiments in which the aerosol delivery device 100 is disposable. Thus, by way of further example, the coupler 150 may comprise a coupler configured for permanent coupling with a cartridge as disclosed in U.S. patent application Ser. No. 14/170,838 to Bless et al., filed Feb. 3, 2014, which is incorporated herein by reference in its entirety.

Conversely in other embodiments the coupler 150 may be configured to releasably engage the cartridge 200 such that the cartridge may be removed therefrom. Thus, for example, the cartridge 200 may be replaced or removed and refilled when it runs out of the aerosol precursor composition. The coupler 150 may be configured to engage the base 214 (see, e.g., FIG. 3) of the cartridge 200. Thus, for example, the coupler 150 may include anti-rotation features that substantially prevent relative rotation between the cartridge 200 and the coupler, and related components such as terminals and electrical contacts as disclosed in U.S. patent application Ser. No. 13/840,264 to Novak et al., filed Mar. 15, 2013, which is incorporated herein by reference in its entirety.

With the cartridge 200 coupled to the connector 106, the user may employ the actuator 110 to move the cartridge to the extended configuration (see, e.g., FIG. 5), as described above. Thereby, a user may draw on the mouthpiece 220 to cause the aerosol delivery device 100 to produce aerosol which is delivered to the user through the mouthpiece. In this regard, as described above, the controller 108 (see, e.g., FIG. 6) may be configured to direct electrical power from the power source 104 to the cartridge 200 to heat the aerosol precursor composition and produce aerosol. As illustrated in FIG. 12, the controller 108 may include a flow sensor 152. The flow sensor 152 may be configured to detect a pressure drop or flow of air associated with a user drawing on the cartridge 200. For example, as illustrated in FIG. 13, the connector 106 may include one or more apertures 153 extending through the coupler 150 in communication with the flow sensor 152. Thereby, as a user draws on the cartridge 200, the resultant pressure drop at the connector 106 may be detected by the flow sensor 152. Accordingly, the controller 108 may direct current to the cartridge 200 to produce aerosol in the manner described above. In one embodiment the flow sensor 152 may be substantially similar to the flow sensor disclosed in U.S. patent application Ser. No. 13/840,264 to Novak et al., filed Mar. 15, 2013, which is incorporated herein by reference in its entirety.

As described above, embodiments of the present disclosure relate to aerosol delivery devices that include a cartridge and a housing, wherein the cartridge is moveable with respect to at least a portion of the housing between an extended configuration and a retracted configuration. Thereby, in the retracted configuration the cartridge may be protected, the aerosol delivery device may define a relatively more compact configuration, and/or various other benefits may be provided as described above. Conversely, the extended configuration of the cartridge may allow for a draw thereon and production of aerosol in a substantially conventional manner.

Although an example embodiment of the aerosol delivery device 100 is described above and illustrated in FIGS. 4-15, aerosol delivery devices including a cartridge configured to move relative to a housing between retracted and extended configurations may be embodied in many other forms. Thus, additional example embodiments of aerosol deliveries including a cartridge moveable relative to a housing between a retracted configuration and an extended configuration are discussed hereinafter. Details with respect to these aerosol delivery devices are limited to differences with respect to the above-described aerosol delivery device 100 for brevity purposes. However, it should be understood that the aerosol delivery devices described below may include some or all of the components described above. Further, for example purposes, the aerosol delivery devices described below are referenced as including a housing and a cartridge including an outer body and a reservoir substrate configured to contain an aerosol precursor composition and an atomizer. In this regard, the aerosol delivery devices are described as including the cartridge 200. This configuration may, for example, allow for replacement of the cartridge when the aerosol precursor composition is expended. However, it should be understood that the various components of the aerosol delivery devices may be distributed between the cartridge and the housing in any manner, and usage of the cartridge 200 is described for example purposes only.

By way of example, FIG. 14 illustrates an aerosol delivery device 300 including a housing 302 and the cartridge 200. An actuator 310 extends out of a side of the housing 302 so as to enable extension and retraction of the cartridge 200 when the actuator slides in first and second opposing directions. In this regard, a connector 306 is moveably attached to the housing 302 (e.g., via the actuator 310) and the cartridge 200 is engaged with the connector so as to be moveable relative to the housing. Thereby, a user may draw on the mouthpiece 220 of the cartridge 200 when the cartridge is in the extended configuration in order to cause passage of an aerosol therethrough to the user. An indicator 316 is positioned at a front of the housing 302. Further, an attachment mechanism 312 is defined by a bottom of the housing 302.

FIG. 15 illustrates an aerosol delivery device 400 including a housing 402 and the cartridge 200. An actuator 410 extends out of a front of the housing 402 so as to cause extension and retraction of the cartridge 200 when the actuator slides in first and second opposing directions. In this regard, a connector 406 is moveably attached to the housing 402 (e.g., via the actuator 410) and the cartridge 200 is engaged with the connector so as to be moveable relative to the housing. Thereby, a user may draw on the mouthpiece 220 of the cartridge 200 when the cartridge is in the extended configuration in order to cause passage of an aerosol therethrough to the user. An indicator 416 is positioned at a top of the housing 402. Further, an attachment mechanism 412 is defined by a corner of the housing 402.

FIGS. 18-20 illustrate an aerosol delivery device 500 including a housing 502 and the cartridge 200. An actuator 506 includes a slider 520 and an external engagement member 524. As illustrated in FIGS. 19 and 20, the slider 520 may be operatively engaged with the cartridge 200. In this regard, a connector 506 is moveably attached to the housing 502 (e.g., via the actuator 510) and the cartridge 200 is engaged with the connector so as to be moveable relative to the housing. Thereby, a user may draw on the mouthpiece 220 of the cartridge 200 when the cartridge is in the extended configuration in order to cause passage of an aerosol therethrough to the user.

In one embodiment the slider 520 may be flexible. For example, the slider 520 may comprise a flexible membrane or a plurality of substantially rigid members serially pivotably connected to one another in a manner similar to the cover portion of a roll top desk. Accordingly, when the external engagement member 524 is moved by a user, the slider 520 may change shape based on a shape of a surrounding structure which guides movement thereof. For example, the movement of the slider 520 and the corresponding change in shape thereof may be guided by the housing 502 in one embodiment.

As illustrated in FIG. 17, the slider 520 may be configured to cover an opening 554 defined in the housing 502 when the cartridge 200 is in the retracted configuration. For example, as illustrated, the opening 554 may be positioned at one or more sides of the housing 502 and the slider 520 may extend along the opening such that the opening is blocked. Thereby, the cartridge 200 may be substantially enclosed in the housing 502 in the retracted configuration as a result of the slider 520 and the housing cooperatively surrounding the cartridge 200. Thus, the mouthpiece 220 of the cartridge 200 may be positioned inside the housing 502 in the retracted configuration such that the mouthpiece is protected from damage and/or contamination.

However, when a user slides the external engagement member 524 (e.g., downwardly in terms of the orientation illustrated in FIGS. 19 and 20) so as to move the cartridge 200 out of the retracted configuration, the slider 520 may retract from at least a portion 554A of the opening 554, as illustrated in FIGS. 18 and 20. Further, the slider 520 may push the cartridge 200 toward the portion 554A of the opening 554 such that the cartridge extends through the opening in the extended configuration, as illustrated in FIGS. 18 and 20. In this regard, due to the slider 520 providing for movement of the cartridge 200 in addition to opening and closing the opening 554, the slider may simultaneously open the opening while directing the cartridge 200 toward and through the opening. This configuration may thus provide a seamless transition between the retracted configuration and the extended configuration which may desirably open the opening and extend the cartridge or close the opening and retract the cartridge without require multiple user inputs.

Additional embodiments of aerosol delivery devices configured to simultaneously open an opening and extend the cartridge therethrough during a transition from a retracted configuration to an extended configuration are also provided. For example, FIG. 19 illustrates an embodiment of an aerosol delivery device 600 including a housing 602 and the cartridge 200. The housing 602 may include a main body portion 602A and a moveable portion 602B defining a lid.

The moveable portion 602B may be pivotably connected to the main body portion 602A by a hinge 656.

Thus, as illustrated in FIG. 20, the moveable portion 602B may pivot with respect to the main body portion 602A to open an opening 654 defined by the main body portion of the housing 602. During pivoting of the housing 602, the cartridge 200 may move from a retracted configuration (see, FIG. 19) to an extended configuration (see, FIG. 20) wherein the cartridge extends through the opening 654. Movement of the cartridge 200 in this manner may be caused by an actuator 610 comprising a connecting mechanism 658 (which is schematically illustrated as a linkage) that couples the cartridge to the moveable portion 602B of the housing 602. Similarly, the connecting mechanism 658 may move the cartridge 200 from the extended configuration back through the opening 654 to the retracted configuration during closing of the moveable portion 602B of the housing 602. In this regard, a connector 606 is moveably attached to the housing 602 and the cartridge 200 is engaged with the connector so as to be moveable relative to the housing. Thereby, a user may draw on the mouthpiece 220 of the cartridge 200 when the cartridge is in the extended configuration in order to cause passage of an aerosol therethrough to the user.

Further, FIG. 21 illustrates an embodiment of an aerosol delivery device 700 including a housing 702 and the cartridge 200. The housing 702 includes a main body portion 702A and a moveable portion 702B defining a lid. The moveable portion 702B may pivot (e.g., rotate) with respect to the main body portion 702A of the housing 702 so as to open an opening 754. The cartridge 200 may simultaneously extend through the opening 754 as the moveable portion 702B rotates. Thereby, the cartridge 200 may move to the extended configuration and be ready for usage follow rotation of the moveable portion 702B.

Conversely, the cartridge 200 may retract back through the opening 754 to a retracted configuration as the moveable portion 702B is rotated to a closed position. Movement of the cartridge 200 in this manner may be caused by a connecting mechanism (e.g., a linkage, not shown) that connects the cartridge to the moveable portion 702B of the housing 702. Accordingly, usage of an actuator, which may comprise a slider or a connecting mechanism, may be employed to simultaneously open an opening and extend a cartridge therethrough, and close an opening and retract the cartridge therethrough, as described above in reference to FIGS. 18-23 in a variety of manners. In this regard, a connector 706 is moveably attached to the housing 702 and the cartridge 200 is engaged with the connector so as to be moveable relative to the housing. Thereby, a user may draw on the mouthpiece 220 of the cartridge 200 when the cartridge is in the extended configuration in order to cause passage of an aerosol therethrough to the user.

Additional embodiments of actuators may be employed in other embodiments. For example, FIG. 22 illustrates an embodiment of an aerosol delivery device 800 including a housing 802 and the cartridge 200. An actuator 810 may be configured to move the cartridge 200 between a retracted configuration and the extended configuration illustrated in FIG. 22. As illustrated, the actuator 810 may include a spring 860, which is illustrated via partial cut-away of the housing 802 and a button 862. The spring 860 may be configured to move the cartridge 200 from the retracted configuration to the extended configuration upon actuation of the button 862. The cartridge 200 may be returned to the retracted configuration by pressing on a longitudinal axis of the cartridge such that the cartridge is directed back inside the housing 802. In this regard, a connector 806 is moveably attached to the housing 802 (e.g., via the actuator 810) and the cartridge 200 is engaged with the connector so as to be moveable relative to the housing. Thereby, a user may draw on the mouthpiece 220 of the cartridge 200 when the cartridge is in the extended configuration in order to cause passage of an aerosol therethrough to the user.

FIG. 23 illustrates an additional embodiment of an aerosol delivery device 900 including a housing 902 and the cartridge 200. In particular, FIG. 23 illustrates the cartridge 200 in a retracted configuration wherein the mouthpiece 220 of the cartridge 200 is optionally at least partially received within the housing 902 such that the cartridge is at least partially protected from damage and contamination.

As illustrated in FIG. 24, the cartridge 200 may be configured to pivot with respect to the housing 902. In this regard, the aerosol delivery device 900 may further comprise a hinge 956. Additionally, a connector 906 is moveably attached to the housing 902 via the hinge 956 and the cartridge 200 is engaged with the connector so as to be moveable relative to the housing. Accordingly, the cartridge 200 may pivot between the retracted configuration and the extended configuration in a manner similar to that employed in a folding pocket knife. In this regard, by way of example, the cartridge may releasably lock in the extended and/or retracted configurations in some embodiments. A user may draw on the mouthpiece 220 of the cartridge 200 when the cartridge is in the extended configuration in order to cause passage of an aerosol therethrough to the user.

An alternate embodiment of an aerosol delivery device 1000 is illustrated in FIG. 25. As illustrated, the aerosol delivery device 1000 may include a housing 1002 and the cartridge 200. A connector 1006 may be attached to the housing 1002 and the cartridge 200 may be engaged with the connector so as to be coupled to the housing, as illustrated in FIG. 26. The cartridge 200 may be removably engaged with the connector 1006 and replaceable.

The housing 1002 may include a main body portion 1002A and a moveable portion 1002B defining a lid. The moveable portion 1002B may be configured to pivot with respect to the main body portion 1002A via a hinge 1056. The cartridge 200 may be configured to remain stationary with respect to the main body portion 1002A of the housing 1002. In this regard, the connector 1006 may be fixedly attached to the main body portion 1002A of the housing 1002.

More particularly, the moveable portion 1002B of the housing 1002 is configured to move with respect to the main body portion 1002A of the housing between a first position (see, FIG. 26) in which the mouthpiece 220 of the cartridge 200 is exposed and a second position (see, FIG. 25) in which the mouthpiece is at least partially received within the moveable portion of the housing. For example, in the illustrated embodiment the mouthpiece 220 of the cartridge 200 is fully received within the moveable portion 1002B of the housing 1002 when the moveable portion is in the second position (see, FIG. 25). Thus, when the moveable portion 1002B is in the second position (see, FIG. 26), the cartridge 200 may define an extended configuration in which the mouthpiece 220 thereof is exposed and configured for receipt of a draw thereon. Conversely, when the moveable portion 1002B is in the first position (see, FIG. 25), the cartridge 200 may define a retracted configuration in which the mouthpiece 220 is relatively closer to the housing 1002 (e.g., relatively closer to the moveable portion 1002B of the housing) than in the extended configuration.

During movement of the moveable portion 1002B the cartridge 200 may be configured to remain stationary with respect to the main body portion 1002A of the housing 1002 while still allowing for transitions of the cartridge between the retracted configuration and the extended configuration in which the mouthpiece 220 is respectively covered and exposed. A user may draw on the mouthpiece 220 of the cartridge 200 when the moveable portion 1002B of the housing 1002 is in the second position (see, FIG. 26) in order to cause passage of an aerosol therethrough to the user. In this regard, power supplied by a power source 1004 positioned within the housing 1002 (e.g., within the main body portion 1002A) may supply power to the cartridge 200.

FIG. 27 illustrates an additional embodiment of an aerosol delivery device 1100. As illustrated, the aerosol delivery device may include a housing 1102 and the cartridge 200. A connector 1106 may be attached to the housing 1102 and the cartridge 200 may be engaged with the connector so as to be coupled to the housing. The cartridge 200 may be removably engaged with the connector 1206 and replaceable.

The housing 1102 may include a main body portion 1102A and a moveable portion 1102B defining a lid. The moveable portion 1102B of the housing 1102 may be configured to translate toward and away from the main body portion 1102A of the housing. The cartridge 200 may be configured to remain stationary with respect to the main body portion 1102A of the housing 1102. In this regard, the connector 1106 may be fixedly attached to the main body portion 1102A of the housing 1102.

More particularly, the moveable portion 1102B of the housing 1102 is configured to move with respect to the main body portion 1102A of the housing between a first position (see, FIG. 28) in which the mouthpiece 220 of the cartridge 200 is exposed and a second position (see, FIG. 27) in which the mouthpiece is at least partially received within the moveable portion of the housing. For example, in the illustrated embodiment the mouthpiece 220 of the cartridge 200 is fully received within the moveable portion 1102B of the housing 1102 when the moveable portion is in the second position (see, FIG. 25). Thus, when the moveable portion 1102B is in the second position (see, FIG. 26), the cartridge 200 may define an extended configuration in which the mouthpiece 220 thereof is exposed and configured for receipt of a draw thereon. Conversely, when the moveable portion 1102B is in the first position (see, FIG. 25), the cartridge 200 may define a retracted configuration in which the mouthpiece 220 is relatively closer to the housing 1002 (e.g., relatively closer to the moveable portion 1102B of the housing) than in the extended configuration.

During movement of the moveable portion 1102B the cartridge 200 may be configured to remain stationary with respect to the main body portion 1102A of the housing 1102 while still allowing for transitions of the cartridge between the retracted configuration and the extended configuration in which the mouthpiece 220 is respectively covered and exposed. A user may draw on the mouthpiece 220 of the cartridge 200 when the moveable portion 1102B of the housing 1102 is in the second position (see, FIG. 26) in order to cause passage of an aerosol therethrough to the user. In this regard, power supplied by a power source 1104 positioned within the housing 1102 (e.g., within the main body portion 1102A) may supply power to the cartridge 200. Note that the embodiments of aerosol delivery devices illustrated in FIGS. 25-28 are configured to resemble lighters employed, for example, to light traditional smoking articles.

Various example shapes and configurations of embodiments of aerosol delivery devices configured to allow for transition of a cartridge between a retracted configuration and an extended configuration are described above. However, it should be understood that a wide variety of embodiments of aerosol delivery devices may include a cartridge configured to move between a retracted configuration and an extended configuration as described above. In this regard, it should be understood that the particular embodiments described herein are provided for example purposes only. Various other embodiments of shapes, designs, and styles may be employed in aerosol delivery devices including a cartridge configured to move relative to at least a portion of a housing between a retracted configuration and an extended configuration. In this regard, examples of various other shapes, styles, and designs which may be employed in accordance with embodiments of the present disclosure include those disclosed in U.S. Pat. No. 8,225,633 to Luo et al.; U.S. Pat. No. 8,341,989 to Hamblin et al.; U.S. Pat. No. 6,902,392 to Johnson; and U.S. Pat. No. 8,342,986 to Rourke et al., each of which is incorporated herein by reference in its entirety.

Further, the aerosol delivery device may be configured to define additional functionality. For example, the housing of the aerosol delivery device may define a key, remote, or remote starter for an automobile, a garage door opener, or other device. In this regard, in some embodiments the aerosol delivery device may define a shape that mimics the traditional shape of such devices (e.g., a key fob). In some embodiments the controller in the device that controls atomization and/or related functions may additionally control any other functions provided by the aerosol delivery device (e.g., remote control functionality, etc). In some embodiments the housing may be non-tubular or non-cylindrical and may be described as defining one or more substantially flat surfaces and/or two or more substantially parallel surfaces in some embodiments. Further, in some embodiments the aerosol delivery device or a portion thereof (e.g., the housing) may comprise first and second outer bodies as disclosed, for example, in U.S. patent application Ser. No. 14/170,838, filed Feb. 3, 2014, to Bless et al., which is incorporated herein by reference.

In the various embodiments of aerosol delivery devices described above, at least a portion of the cartridge (e.g., the mouthpiece) may be received in the housing in a retracted configuration. This configuration may protect the mouthpiece from exposure to contaminants when the aerosol delivery device is not in use. In some embodiments the aerosol delivery devices of the disclosure may include additional features configured to improve the cleanliness associated with usage thereof. In this regard, in one embodiment the aerosol delivery device may be configured to sterilize the cartridge or a portion thereof (e.g., the mouthpiece). For example, the aerosol delivery device may include an ultraviolet emitter (e.g., an ultraviolet light emitting diode) configured to emit ultraviolet light which may kill microorganisms such as pathogens, viruses and molds.

In this regard, the aerosol delivery device 100 illustrated in FIG. 1 includes an ultraviolet emitter 196 configured to emit ultraviolet light. By way of example, as illustrated, the ultraviolet emitter 196 may be configured and positioned to direct ultraviolet light at the mouthpiece 220 of the cartridge 200 when the cartridge is in the retracted configuration. The ultraviolet emitter 196 may be configured to direct the ultraviolet light at substantially the entirety of the external surface of the mouthpiece 220 and/or inner surfaces thereof along a flow path extending therethrough. In this regard, in some embodiments the aerosol delivery device may include multiple ultraviolet emitters and/or an ultraviolet reflector or reflective coating may be positioned within the housing 102 such that it substantially surrounds the mouthpiece 220 when the cartridge 200 is retracted into the housing and thereby reflects the ultraviolet light around and against the periphery of the mouthpiece.

In one embodiment the ultraviolet emitter 196 may be configured to automatically emit ultraviolet radiation at the mouthpiece 220 when the cartridge 200 is moved to the retracted configuration. For example, the ultraviolet emitter 196 may emit ultraviolet light each time the cartridge 200 is retracted, upon the occurrence of a selected number of retractions of the cartridge, upon passage of a predetermined period of time, upon usage of a predetermined portion of the aerosol precursor composition, or based upon any other factor. Alternatively or additionally, the ultraviolet emitter 196 may be manually activated by a user. As may be understood, the above-noted ultraviolet emitter may be included in any of the aerosol delivery devices disclosed herein. Example embodiments of ultraviolet emitters are available from Digi-Key Corp. of Thief River Falls, Minn.

As noted above, in some embodiments the aerosol delivery device may be configured to activate an ultraviolet emitter upon retraction of the cartridge into the housing. In this regard, in some embodiments the aerosol delivery device may include a cartridge position sensor (e.g., a switch) configured to detect when the cartridge is retracted. Alternatively or additionally, the cartridge position sensor may be configured to detect when the cartridge is extended. The cartridge position sensor may be configured to transmit a signal to the controller indicating whether the cartridge is retracted or extended. Thereby, the controller may employ the signal from the cartridge position sensor to determine when to sanitize the cartridge as described above or to perform various other functions such as preheating the heater when the cartridge is extended.

Additionally, the movement of the cartridge in the above-described embodiments may be controlled in one or more manners. In this regard, the extension or retraction of the cartridge may be resisted or assisted in one or more manners. For example, the aerosol delivery device 800 illustrated in FIG. 22 includes the spring 860, which is configured to assist extension of the cartridge 200. The spring 860 may also resist movement of the cartridge 200 during retraction. Further, in some embodiments the aerosol delivery devices may include a damper mechanism configured to dampen movement of the cartridge (e.g., by damping movement caused by a spring).

In this regard, the damper mechanism may me coupled to the connector and configured to dampen the movement thereof (e.g., during extension of the cartridge in embodiments of the aerosol delivery device wherein the cartridge is extended by an actuator). For example, a damper mechanism may be employed in the aerosol delivery device of FIG. 21, such that the cartridge 200 slowly extends (e.g., as caused by a spring) after the moveable portion 702B of the lid 702 is opened. Use of a damper mechanism may provide a satisfying user experience by providing slow, controlled movement of the cartridge. An example embodiment of a damper mechanism is a gear damper mechanism as described in U.S. Pat. No. 7,959,201 to Staib, which is incorporated herein by reference in its entirety.

Various other embodiments of actuators may be employed in the embodiments of aerosol delivery devices disclosed herein, including various automated embodiments of actuators. For example, in one embodiment a motor and a lead screw may be employed to extend and retract the cartridge. Further, in some embodiments the aerosol delivery devices may include a lock mechanism that selectively allows for extension of the cartridge. For example, the lock mechanism may comprise a solenoid that allows the cartridge to move only when actuated. Further, the controller may require entry of a code or other information (e.g., a fingerprint or other biometric information) prior to actuating the solenoid to release the cartridge. Further in embodiments including automated actuators configured to extend the cartridge, the controller may prevent extension in a similar manner by, for example, disallowing operation of a motor and drive screw prior to entry of a code or other such information. Thereby, for example, the aerosol delivery devices may include a child lock function and/or otherwise prevent unauthorized use.

Various materials may be employed in the aerosol delivery devices of the present disclosure. By way of example, in one embodiment the slider 120 may comprise brass and the track 122 may comprise steel in order to provide the actuator 110 (see, e.g., FIG. 8) with a strong and durable configuration. However, metals (e.g., steel, aluminum, or titanium), plastics, ceramics, composites, and other materials may be employed in any of the various components described herein unless stated otherwise herein. Further, the housing may be formed from any of a variety of materials including, for example, metal and/or plastic.

A method for assembling a cartridge for an aerosol delivery device is also provided. As illustrated in FIG. 29, the method may include providing an atomizer, a reservoir configured to contain an aerosol precursor composition, a housing, and a cartridge comprising a mouthpiece at operation 1202. Further, the method may include positioning the atomizer in the cartridge or the housing at operation 1204. The method may additionally include positioning the reservoir in the cartridge or the housing at operation 1206. The method may further comprise operatively engaging the cartridge with the housing such that the cartridge is moveable relative to at least a portion of the housing between an extended configuration in which the mouthpiece is exposed and a retracted configuration in which the mouthpiece is relatively closer to the housing than in the extended configuration at operation 1208.

In some embodiments positioning the reservoir in the cartridge or the housing at operation 1206 may comprise positioning the reservoir in the cartridge. Further, positioning the atomizer in the cartridge or the housing at operation 1204 may comprise positioning the atomizer in the cartridge. Operatively engaging the cartridge with the housing at operation 1408 may comprise coupling the cartridge to an actuator, the actuator being configured to move the cartridge between the extended configuration and the retracted configuration. Coupling the cartridge to the actuator may include inserting a slider at least partially within the housing, the slider being configured to cover an opening in the housing in the retracted configuration such that the cartridge is substantially enclosed in the housing and further configured to retract from at least a portion of the opening to allow the cartridge to extend through the opening in the extended configuration. The method may additionally include pivotably coupling a main body portion of the housing to a moveable portion of the housing. Further, operatively engaging the cartridge with the housing at operation 1208 may comprise pivotably coupling the cartridge to the housing.

In an additional embodiment, FIG. 30 illustrates a method for assembling an aerosol delivery. As illustrated, the method may include providing a housing, an actuator, and a connector comprising a coupler configured to engage a cartridge comprising atomizer and a reservoir containing an aerosol precursor composition at operation 1302. Further, the method may include coupling the connector to the actuator at operation 1304. The method may additionally include at least partially inserting the connector and the actuator within the housing such that the actuator is configured to move the cartridge relative to at least a portion of the housing between an extended configuration and a retracted configuration at operation 1306.

In some embodiments the method may further comprise inserting a power source into the housing. Additionally, the method may include inserting a controller into the housing. The controller may be configured to direct electrical power from the power source to the cartridge to heat the aerosol precursor composition retained in the reservoir with the atomizer to produce an aerosol. The method may further comprise assembling the actuator, wherein assembling the actuator comprises engaging a slider with a track. Assembling the actuator may further comprise coupling an external engagement member to the slider. The external engagement member may be configured for engagement by a user to move the slider.

A further embodiment of a method for assembling an aerosol delivery device is illustrated in FIG. 31. As illustrated, the method may include providing a housing, a power source, and a connector configured to engage a cartridge comprising an outer body with a mouthpiece configured for passage of an aerosol therethrough at operation 1402. The method may additionally include positioning the power source within the housing at operation 1404. Further, the method may include moveably attaching the connector to the housing such that the connector is configured to move the cartridge relative to at least a portion of the housing at operation 1406.

In some embodiments the method may additionally include engaging the cartridge with the connector. Further, the method may include coupling the connector to an actuator. The actuator may be configured to move the cartridge between an extended configuration and a retracted configuration. Additionally, the method may include assembling the actuator. Assembling the actuator may include engaging a slider with a track. Assembling the actuator may further comprise coupling an external engagement member to the slider. The external engagement member may be configured for engagement by a user to move the slider.

In another embodiment a controller 1500 is provided, as illustrated in FIG. 32. The controller may be configured to execute computer code for performing the operations described herein. In this regard, as illustrated in FIG. 32, the controller 1500 may comprise a processor 1502 that may be a microprocessor or a controller for controlling the overall operation thereof. In one embodiment the processor 1502 may be particularly configured to execute program code instructions related to the functions described herein, including the operations for assembling the aerosol delivery devices or portions thereof of the present disclosure. The controller 1500 may also include a memory device 1504. The memory device 1504 may include non-transitory and tangible memory that may be, for example, volatile and/or non-volatile memory. The memory device 1504 may be configured to store information, data, files, applications, instructions or the like. For example, the memory device 1504 could be configured to buffer input data for processing by the processor 1502. Additionally or alternatively, the memory device 1504 may be configured to store instructions for execution by the processor 1502.

The controller 1500 may also include a user interface 1506 that allows a user to interact therewith. For example, the user interface 1506 can take a variety of forms, such as a button, keypad, dial, touch screen, audio input interface, visual/image capture input interface, input in the form of sensor data, etc. Still further, the user interface 1506 may be configured to output information to the user through a display, speaker, or other output device. Referring to FIG. 5, the display 118 may comprise the user interface 1506. A communication interface 1508 may provide for transmitting and receiving data through, for example, a wired or wireless network 1510 such as a local area network (LAN), a metropolitan area network (MAN), and/or a wide area network (WAN), for example, the Internet. The communication interface 1508 may enable the controller 1500 to communicate with one or more further computing devices, either directly, or via the network 1510. In this regard, the communication interface 1508 may include one or more interface mechanisms for enabling communication with other devices and/or networks. The communication interface 1508 may accordingly include one or more interface mechanisms, such as an antenna (or multiple antennas) and supporting hardware and/or software for enabling communications via wireless communication technology (e.g., a cellular technology, communication technology, Wi-Fi and/or other IEEE 802.11 technology, Bluetooth, Zigbee, wireless USB, NFC, RF-ID, WiMAX and/or other IEEE 802.16 technology, and/or other wireless communication technology) and/or a communication modem or other hardware/software for supporting communication via cable, digital subscriber line (DSL), USB, FireWire, Ethernet, one or more optical transmission technologies, and/or other wireline networking methods. Further, the controller 1500 may include an assembly module 1512. The assembly module 1512 may be configured to, in conjunction with the processor 1502, direct operations for assembling an aerosol delivery device or a portion thereof as described herein. Non-limiting examples of communication protocols that may be used according to the present disclosure are described in U.S. patent application Ser. No. 14/327,776 to Ampolini et al., filed Jul. 10, 2014, which is incorporated herein by reference in its entirety.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling the above-described operations. In particular, computer readable code may be configured to perform each of the operations of the methods described herein and embodied as computer readable code on a computer readable medium for controlling the above-described operations. In this regard, a computer readable storage medium, as used herein, refers to a non-transitory, physical storage medium (e.g., a volatile or non-volatile memory device, which can be read by a computer system. Examples of the computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

As noted above, the controller 1500 may be configured to execute computer code for performing the above-described assembly operations. In this regard, an embodiment of a non-transitory computer readable medium for storing computer instructions executed by a processor in a controller (e.g. controller 1500) configured to assemble an aerosol delivery device is provided. The non-transitory computer readable medium may comprise program code instructions for providing an atomizer, a reservoir configured to contain an aerosol precursor composition, a housing, and a cartridge comprising a mouthpiece; program code instructions for positioning the atomizer in the cartridge or the housing; program code instructions for positioning the reservoir in the cartridge or the housing; and program code instructions for operatively engaging the cartridge with the housing such that the cartridge is moveable relative to at least a portion of the housing between an extended configuration in which the mouthpiece is exposed and a retracted configuration in which the mouthpiece is relatively closer to the housing than in the extended configuration.

In some embodiments the program code instructions for positioning the reservoir in the cartridge or the housing may comprise program code instructions for positioning the reservoir in the cartridge. The program code instructions for positioning the atomizer in the cartridge or the housing may comprise program code instructions for positioning the atomizer in the cartridge. The program code instructions for operatively engaging the cartridge with the housing may comprise program code instructions for coupling the cartridge to an actuator, the actuator being configured to move the cartridge between the extended configuration and the retracted configuration. Further, the program code instructions for coupling the cartridge to the actuator may comprise program code instructions for inserting a slider at least partially within the housing, the slider being configured to cover an opening in the housing in the retracted configuration such that the cartridge is substantially enclosed in the housing and further configured to retract from at least a portion of the opening to allow the cartridge to extend through the opening in the extended configuration. The non-transitory computer readable medium may further comprise program code instructions for pivotably coupling a main body portion of the housing to a moveable portion of the housing. The program code instructions for operatively engaging the cartridge with the housing may comprise program code instructions for pivotably coupling the cartridge to the housing.

In an additional embodiment a non-transitory computer readable medium for storing computer instructions executed by a processor in a controller (e.g. controller 1500) configured to assemble an aerosol delivery device is provided. The non-transitory computer readable medium may comprise program code instructions for providing a housing, an actuator, and a connector comprising a coupler configured to engage a cartridge comprising atomizer and a reservoir containing an aerosol precursor composition; program code instructions for coupling the connector to the actuator; and program code instructions for at least partially inserting the connector and the actuator within the housing such that the actuator is configured to move the cartridge relative to at least a portion of the housing between an extended configuration and a retracted configuration.

In some embodiments the non-transitory computer readable medium may further comprise program code instructions for inserting a power source into the housing. The non-transitory computer readable medium may further comprise program code instructions for inserting a controller into the housing. The controller may be configured to direct electrical power from the power source to the cartridge to heat the aerosol precursor composition retained in the reservoir with the atomizer to produce an aerosol. The non-transitory computer readable medium may further comprise program code instructions for assembling the actuator, wherein assembling the actuator comprises engaging a slider with a track. The computer program instructions for assembling the actuator may further comprise program code instructions for coupling an external engagement member to the slider, the external engagement member being configured for engagement by a user to move the slider.

In an additional embodiment a non-transitory computer readable medium for storing computer instructions executed by a processor in a controller (e.g. controller 1500) configured to assemble an aerosol delivery device is provided. The non-transitory computer readable medium may comprise program code instructions for providing a housing, a power source, and a connector configured to engage a cartridge comprising an outer body with a mouthpiece configured for passage of an aerosol therethrough. Additionally, the non-transitory computer readable medium may comprise program code instructions for positioning the power source within the housing. Further, the non-transitory computer readable medium may comprise program code instructions for moveably attaching the connector to the housing such that the connector is configured to move the cartridge relative to at least a portion of the housing.

In some embodiments the non-transitory computer readable medium may further comprise program code instructions for engaging the cartridge with the connector. Additionally, the non-transitory computer readable medium may comprise program code instructions for coupling the connector to an actuator, the actuator being configured to move the cartridge between an extended configuration and a retracted configuration. Further, the non-transitory computer readable medium may comprise program code instructions for assembling the actuator, wherein the program code instructions for assembling the actuator comprise program code instructions for engaging a slider with a track. The program code instructions for assembling the actuator may further comprise program code instructions for coupling an external engagement member to the slider, the external engagement member being configured for engagement by a user to move the slider.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:
1. An aerosol delivery device, comprising:
a connector moveably attached to a housing; and
an actuator coupled to the connector and configured to move a cartridge between an extended configuration in which a mouthpiece of the cartridge is exposed and a retracted configuration in which the mouthpiece is relatively closer to the housing than in the extended configuration,
wherein the connector is arranged to form an electrical connection between the cartridge and a controller within the housing.

2. The aerosol delivery device of claim 1, wherein the cartridge comprises a reservoir configured to retain an aerosol precursor composition.

3. The aerosol delivery device of claim 2, wherein the controller is configured to direct electrical power from a power source positioned within the housing to the cartridge to heat the aerosol precursor composition retained in the reservoir with an atomizer to produce an aerosol.

4. The aerosol delivery device of claim 1, wherein the cartridge is removably engaged with the connector and replaceable.

5. The aerosol delivery device of claim 1, wherein the actuator comprises a slider.

6. The aerosol delivery device of claim 5, wherein the slider is configured to cover an opening defined in the housing when the cartridge is in the retracted configuration such that the cartridge is substantially enclosed in the housing and further configured to retract from at least a portion of the opening to allow the cartridge to extend through the opening in the extended configuration.

7. The aerosol delivery device of claim 5, wherein the actuator comprises the slider being formed as a flexible membrane and an external engagement member, the flexible membrane being surrounded by the housing and having a shape based on a shape of the housing, such that movement of the external engagement member causes the shape of the flexible membrane to change to correspond to the shape of the housing.

8. The aerosol delivery device of claim 1, wherein the actuator comprises a spring and a button, the spring being configured to move the cartridge from the retracted configuration to the extended configuration upon actuation of the button.

9. The aerosol delivery device of claim 1, wherein the mouthpiece is positioned inside the housing in the retracted configuration.

10. A method for assembling an aerosol delivery device, comprising:
moveably attaching a connector to a housing;
forming, by the connector, an electrical connection between a cartridge and a controller within the housing;
coupling the connector to an actuator;
at least partially inserting the connector and the actuator within the housing such that the actuator is configured to move the cartridge between an extended configuration in which a mouthpiece of the cartridge is exposed and a retracted configuration in which the mouthpiece is relatively closer to the housing than in the extended configuration.

11. The method of claim 10, further comprising providing the cartridge, the cartridge comprising the mouthpiece, a reservoir configured to retain an aerosol precursor composition, and an atomizer to heat the aerosol precursor composition to produce an aerosol.

12. The method of claim 11, further comprising positioning the controller and a power source in the housing,
wherein the controller is configured to direct electrical power from the power source to the cartridge to heat the aerosol precursor composition retained in the reservoir with the atomizer to produce the aerosol.

13. The method of claim 10, further comprising removably engaging the cartridge with the connector, the cartridge being replaceable.

14. The method of claim 10, wherein coupling the connector to the actuator comprises coupling the connector to a slider.

15. The method of claim 14, further comprising engaging the slider with the housing, the slider being configured to cover an opening defined in the housing when the cartridge is in the retracted configuration such that the cartridge is substantially enclosed in the housing and further configured to retract from at least a portion of the opening to allow the cartridge to extend through the opening in the extended configuration.

16. The method of claim 14, further comprising engaging the slider being formed as a flexible membrane and an external engagement member with the housing, the flexible membrane being surrounded by the housing and having a shape based on a shape of the housing, the external engagement member being configured to move and cause the shape of the flexible membrane to change to correspond to the shape of the housing.

17. The method of claim 10, wherein coupling the connector to the actuator comprises coupling the connector to a spring and a button, the spring being configured to move the cartridge from the retracted configuration to the extended configuration upon actuation of the button.

18. The method of claim 10, wherein at least partially inserting the connector and the actuator within the housing comprises at least partially inserting the connector and the actuator within the housing so that the mouthpiece is positioned inside the housing in the retracted configuration.

* * * * *